US010921314B2

(12) United States Patent
Shepard et al.

(10) Patent No.: US 10,921,314 B2
(45) Date of Patent: Feb. 16, 2021

(54) METHOD OF MAKING AN INTEGRATED CIRCUIT FOR A SINGLE-MOLECULE NUCLEIC-ACID ASSAY PLATFORM

(71) Applicant: The Trustees of Columbia University in the City of New York, New York, NY (US)

(72) Inventors: Kenneth L. Shepard, Ossining, NY (US); Steven Warren, White Plains, NY (US); Scott Trocchia, Edgewater, NJ (US); Yoonhee Lee, New York, NY (US); Erik Young, Tappan, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/427,749

(22) Filed: May 31, 2019

(65) Prior Publication Data

US 2019/0317084 A1 Oct. 17, 2019

Related U.S. Application Data

(60) Continuation-in-part of application No. 15/799,044, filed on Oct. 31, 2017, now Pat. No. 10,401,353,
(Continued)

(51) Int. Cl.
*G01N 33/00* (2006.01)
*G01N 33/53* (2006.01)
(Continued)

(52) U.S. Cl.
CPC .... *G01N 33/5308* (2013.01); *B01L 3/502707* (2013.01); *B01L 7/52* (2013.01); *B82Y 10/00* (2013.01); *G01N 27/4145* (2013.01); *G01N 27/4146* (2013.01); *H01L 51/0002* (2013.01); *H01L 51/0048* (2013.01);
(Continued)

(58) Field of Classification Search
CPC ............. H01L 29/0673; H01L 51/0002; H01L 51/0048
See application file for complete search history.

(56) References Cited

U.S. PATENT DOCUMENTS

2007/0134866 A1* 6/2007 Huang ................ H01L 29/0665
438/199
2009/0208922 A1* 8/2009 Choi .................. G01N 27/4146
435/4

(Continued)

*Primary Examiner* — Caridad Everhart
*Assistant Examiner* — Ankush K Singal
(74) *Attorney, Agent, or Firm* — Intrinsic Law Corp.

(57) ABSTRACT

Methods of making an integrated circuit for a single-molecule nucleic-acid assay platform. In one example, the method includes adhering a carbon nanotube to a surface of a transfer film, the transfer film comprising gold or a polymer; placing the surface of the transfer film on a CMOS integrated circuit; releasing the carbon nanotube from the transfer film; and forming a pair of post-processed electrodes proximate opposing ends of the carbon nanotube, the post-processed electrodes electrically connecting the carbon nanotube to the CMOS integrated circuit. The method can also include exposing the carbon nanotube to a diazonium salt solution to form a point defect on a portion of the carbon nanotube.

30 Claims, 17 Drawing Sheets

Specification includes a Sequence Listing.

50

510 Place carbon nanotube suspension on surface of CMOS integrated circuit

520 Evaporate liquid from carbon nanotube suspension

530 Deposit carbon nanotubes from CNT suspension on surface of CMOS integrated circuit 540 Deposit and pattern metal on CNTs and electrodes to form post-processed electrodes

Related U.S. Application Data which is a division of application No. 14/509,766, filed on Oct. 8, 2014, now Pat. No. 9,841,416, which is a continuation of application No. PCT/US2013/031745, filed on Mar. 14, 2013.

(60) Provisional application No. 61/636,459, filed on Apr. 20, 2012, provisional application No. 61/680,094, filed on Aug. 6, 2012, provisional application No. 62/679,487, filed on Jun. 1, 2018.

(51) Int. Cl.

| | |
|---|---|
| ***B01L 3/00*** | (2006.01) |
| ***B01L 7/00*** | (2006.01) |
| ***G01N 27/414*** | (2006.01) |
| ***B82Y 10/00*** | (2011.01) |
| ***H01L 51/00*** | (2006.01) |
| *H01L 29/775* | (2006.01) |
| *B82Y 40/00* | (2011.01) |
| *H01L 23/00* | (2006.01) |
| *B82Y 15/00* | (2011.01) |
| *H01L 51/05* | (2006.01) |
| *H01L 29/06* | (2006.01) |

(52) U.S. Cl.

CPC . *H01L 51/0049* (2013.01); *B01J 2219/00653* (2013.01); *B01J 2219/00722* (2013.01); *B01L 2300/0645* (2013.01); *B01L 2300/0663* (2013.01); *B01L 2300/0887* (2013.01); *B01L 2300/0896* (2013.01); *B01L 2300/1827* (2013.01); *B82Y 15/00* (2013.01); *B82Y 40/00* (2013.01); *H01L 24/48* (2013.01); *H01L 29/0673* (2013.01); *H01L 29/775* (2013.01); *H01L 51/0558* (2013.01); *H01L 2224/45015* (2013.01); *H01L 2224/45099* (2013.01); *H01L 2224/45144* (2013.01); *H01L 2224/48227* (2013.01); *H01L 2924/00* (2013.01); *H01L 2924/00014* (2013.01); *H01L 2924/12032* (2013.01); *H01L 2924/207* (2013.01)

(56) References Cited

U.S. PATENT DOCUMENTS

| | | | | |
|---|---|---|---|---|
| 2010/0101956 | A1 * | 4/2010 | Choi | C12Q 1/6825<br>204/547 |
| 2011/0244585 | A1 * | 10/2011 | Mayne-L'Hermite | B82Y 30/00<br>436/93 |
| 2012/0021164 | A1 * | 1/2012 | Sansom | B29C 70/64<br>428/95 |
| 2012/0060826 | A1 * | 3/2012 | Weisenberger | C08J 5/005<br>126/569 |
| 2013/0072669 | A1 * | 3/2013 | Wang | C07C 51/353<br>536/23.1 |
| 2018/0059728 | A1 * | 3/2018 | Kim | H01L 51/0097 |

* cited by examiner

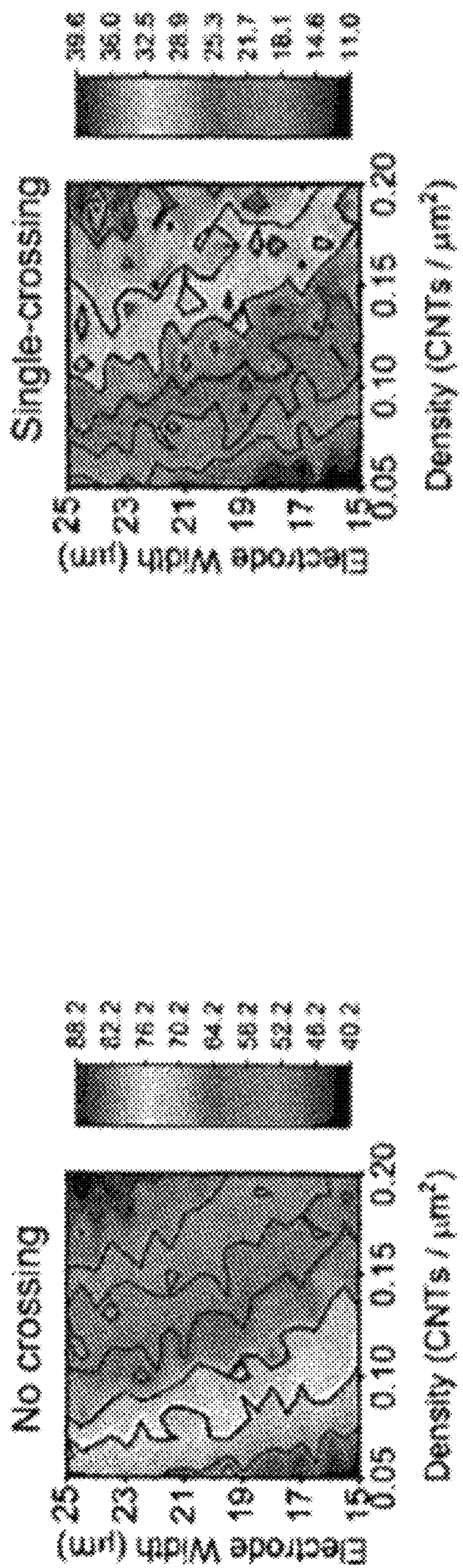
FIG. 7B
FIG. 7A
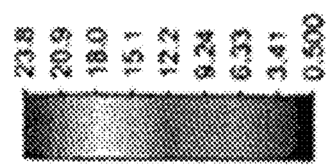
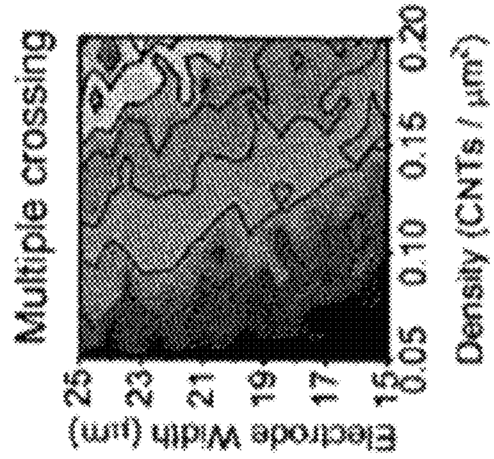
FIG. 7C

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

gtgagttgtt                                                            10


<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

aacaactcac                                                            10


<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

aacaactc                                                               8


<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

aacaactca                                                              9
```

METHOD OF MAKING AN INTEGRATED CIRCUIT FOR A SINGLE-MOLECULE NUCLEIC-ACID ASSAY PLATFORM

CROSS-REFERENCE TO RELATED APPLICATIONS

This application is a continuation-in-part of U.S. patent application Ser. No. 15/799,044, filed on Oct. 31, 2017, which is a divisional of U.S. patent application Ser. No. 14/509,766, filed on Oct. 8, 2014, which is a continuation of PCT/US2013/031745, filed on Mar. 14, 2013, which claims priority to U.S. Provisional Patent Application No. 61/636,459, filed on Apr. 20, 2012, and to U.S. Provisional Patent Application No. 61/680,094, filed on Aug. 6, 2012. This application also claims priority to U.S. Provisional Patent Application No. 62/679,487, filed on Jun. 1, 2018. Each of which the foregoing applications is incorporated by reference herein in its entirety.

STATEMENT REGARDING FEDERALLY-SPONSORED RESEARCH

This invention was made with government support under grant 0707748 awarded by the National Science Foundation, grants HG006879 and HG006882 awarded by the National Institutes of Health, and grant HR0011-15-2-0054 awarded by the Defense Advanced Research Projects Agency. The government has certain rights in the invention.

SEQUENCE LISTING

This application contains a Sequence Listing, which has been submitted electronically in ASCII format and is hereby incorporated by reference in its entirety. Said ASCII copy, created on Oct. 31, 2017, is named 070050 5993 SL.txt and is 1,370 bytes in size.

TECHNICAL FIELD

The disclosed subject matter relates to single-molecule nucleic-acid assay platforms, including techniques for making integrated circuits for single-molecule nucleic-acid assay platforms.

BACKGROUND

Certain single molecule measurement techniques can enable quantitative measurement of intra- and intermolecular interaction kinetics. The strengths of these methods include their ability to report rare intermediate states along reaction pathways which are otherwise averaged out in the ensemble measurements and the ability to yield information on the biological mechanism underlying the interaction. The information from these measurements can provide detailed information on protein structural dynamics, DNA hybridization, and DNA and protein recognition, providing new insights into chemical, mechanical, and structural characteristics of biomolecules. In the case of certain genomic analysis, single molecule experiments can allow quantitative detection of genomic target without labelling or amplification as diagnostic platform.

The limitations of certain single-molecule measurement technologies include short observation times and narrow bandwidth in transducer and measurement electronics. The observation time in fluorescence-based approaches, such as single molecule Förster resonance energy transfer (smFRET), is limited by photo-bleaching of fluorophores. Measurement bandwidths are limited by achievable signal-to-noise ratios (SNRs). Fluorescence emission of single optical reporters is typically on the scale of only 1,000-4,000 photons/sec under normal excitation powers, requiring integration times in imagers on the millisecond time scale. Mechanical single-molecule approaches can offer longer observation times, and recent high-speed single molecule force spectroscopy techniques have achieved microsecond time scales. However, it can be necessary to attach cantilevers to the molecules in question, and measurement scaling to massively parallel formats is not necessarily easily achieved. Both optical and mechanical approaches can require sophisticated and expensive instrumentation, impeding broader application of these tools.

Point-functionalized single-walled carbon nanotube (SWCNT) devices have emerged as an all-electronic, label-free, single-molecule detection platform. This single-molecule field-effect transistor (smFET) can be characterized by a conductance that is sensitive to charges localized within a few Debye lengths of a point defect that is generated on the SWCNT sidewall. Certain systems employing smFETs transduce interactions directly with bandwidths in excess of 1 MHz over a virtually unlimited observation time. Single-molecule experiments with smFET have included studies of the dynamics of DNA hybridization, G-quadruplex conformation changes, and lysozyme activity, and these findings harmonize with results from fluorescence=based and force-based experiments. In contrast with these other approaches, the smFET can provide for a label-free, low-cost, and scalable miniaturized platform.

The scope of smFET applications has still been restricted by the low yield of fabrication. In particular, detailed statistics resulting from the ability to analyze data from many different devices is lacking. Large arrays of smFETs will enable parallelization and scale useful for many applications.

An additional restriction to broader smFET use is inefficiency in the point functionalization of the FET channel. Transient, singular, non-covalent probe attachment have been pursued using pyrenes or porphyrins exploiting n-n stacking of these molecules with the carbon rings of the SWCNT. Reuse of devices is possible in this case, since the attached probe can be removed, at the cost of instability in the attachment.

A covalent attachment strategy can offer desirable permanent tethering of probe molecules as well as localization of charge-sensitivity for the device at the point of attachment. Certain covalent modification methods can include aryl radical, nucleophilic, and electrophilic additions, which can impart a measurable resistance change in the device by converting carbon bonding from $sp^2$ to $sp^3$ orientation rather than by removing carbon atoms from the lattice. There have been a few attempts to regulate these reactions to produce a single $sp^3$ defect, either by employing nano-wells or by controlling the potential between the SWCNT and the surrounding electrolyte during the chemical reaction. Confining conjugation chemistry with nano-wells requires electron-beam patterning of a thin layer of resist to form a well in which the $sp^3$ reaction can occur. With nano-wells as narrow as 20 nm, the yield for $sp^3$ defect generation has been close to 70%.

Certain other electrochemical potential methods can function by applying solution bias to promote or inhibit electron transfer between a charged moiety and the carbon nanotube lattice, and the associated electrical resistance change due to the addition of a single spa defect has been argued to be on the order of $h/4e^2$. However, previous efforts at controlling these reactions have been limited by the ability to terminate the reaction reliably after single defect generation, reducing the yield of single defects.

Nucleic acid assays can have many applications, including, but not limited to, gene expression studies, environmental monitoring, and infectious disease recognition. Furthermore, polymerase chain reaction (PCR) can facilitate detection and quantitation of products. However, PCR can be challenging to implement in multiplexed analyses, at least in part because primer interactions can reduce sensitivity and the repertoire of reporter systems can allow for up to 10 to 20 targets. Sample preparation can include, for example, multiple stages of thermal cycling and precise control of enzymatic conditions.

In contrast, DNA microarray technology can allow for extensive multiplexing, but sensitivities can be too low to allow detection without amplification. As such, DNA microarray technology can also present the similar sample preparation complexities to PCR. With direct sequencing approaches, DNA can be directly sequenced for identification, but sensitivities can be too low to allow detection without amplification, and such techniques can be unsuitable for point-of-care diagnostics.

Accordingly, there remains an opportunity for single-molecule nucleic-acid assay platforms that can provide improved levels of sensitivity without amplification, while also providing improved multiplexing capabilities.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a method of making an integrated circuit for a single-molecule nucleic-acid assay platform, comprising: adhering a carbon nanotube to a surface of a transfer film; placing the surface of the transfer film on a CMOS integrated circuit; releasing the carbon nanotube from the transfer film; and forming a pair of post-processed electrodes proximate opposing ends of the carbon nanotube, the post-processed electrodes electrically connecting the carbon nanotube to the CMOS integrated circuit.

In one or more embodiments, the transfer film comprises gold or a polymer. In one or more embodiments, the method further comprises chemically removing the transfer film to release the carbon nanotube. In one or more embodiments, chemically removing the transfer film comprises wet etching the transfer film, and the transfer film comprises gold. In one or more embodiments, chemically removing the transfer film comprises soaking the CMOS integrated circuit in an organic solvent, and the transfer film comprises a polymer.

In one or more embodiments, the method further comprises placing the nanotube on a transfer substrate; depositing the transfer film on the transfer substrate; and lifting off the transfer film from the transfer substrate, the transfer film comprising the nanotube. In one or more embodiments, the method further comprises growing the nanotube on the transfer substrate. In one or more embodiments, the transfer film comprises a polymer, and depositing the transfer film comprises spinning the polymer onto the transfer substrate. In one or more embodiments, the transfer film comprises gold, and depositing the transfer film comprises physical vapor depositing and/or electroplating the gold onto the transfer substrate.

In one or more embodiments, forming the pair of post-processed electrodes comprises depositing titanium, palladium, gold, platinum, silver, chromium, and/or aluminum on a pair of surface-exposed electrodes. In one or more embodiments, forming the pair of post-processed electrodes comprises etching away a pair of surface-exposed electrodes and replacing the pair of surface-exposed electrodes with a pair of electrodes that comprise titanium, palladium, gold, platinum, silver, chromium, and/or aluminum. In one or more embodiments, the method further comprises forming one or more reference electrodes on the CMOS integrated circuit to allow control of an electrolytic gating potential. In one or more embodiments, the one or more reference electrodes comprise platinum, palladium, and/or silver. In one or more embodiments, the one or more reference electrodes comprise a silver electrode, and the silver electrode is converted into a silver-chloride electrode.

Another aspect of the invention is directed to a method of making an integrated circuit for a single-molecule nucleic-acid assay platform, comprising: disposing a carbon nanotube suspension on the surface of the CMOS integrated circuit, the carbon nanotube suspension comprising a liquid and carbon nanotubes; evaporating the liquid from the carbon nanotube suspension to deposit the carbon nanotubes on the surface of the CMOS integrated circuit; and forming a pair of post-processed electrodes proximate opposing ends of one or more of the carbon nanotubes, the post-processed electrodes electrically connecting the one or more carbon nanotubes to the CMOS integrated circuit.

In one or more embodiments, the method further comprises spin-coating the surface of the CMOS integrated circuit with the carbon nanotube suspension. In one or more embodiments, the method further comprises spraying the carbon nanotube suspension onto the surface of the CMOS integrated circuit. In one or more embodiments, the method further comprises rasterizing the CMOS integrated circuit and/or a spray nozzle during the spraying. In one or more embodiments, the method further comprises spraying the carbon nanotube suspension from a print head nozzle or an ultrasonic nozzle. In one or more embodiments, the method further comprises heating the CMOS integrated circuit to evaporate the liquid from the carbon nanotube suspension.

In one or more embodiments, forming the pair of post-processed electrodes comprises depositing titanium, palladium, gold, platinum, silver, chromium, and/or aluminum on a pair of surface-exposed electrodes. In one or more embodiments, forming the pair of post-processed electrodes comprises etching away a pair of surface-exposed electrodes and replacing the pair of surface-exposed electrodes with a pair of electrodes that comprise titanium, palladium, gold, platinum, silver, chromium, and/or aluminum.

In one or more embodiments, the method further comprises forming one or more reference electrodes on the CMOS integrated circuit to allow control of an electrolytic gating potential. In one or more embodiments, the one or more reference electrodes comprise platinum, palladium, and/or silver. In one or more embodiments, the one or more reference electrodes comprise a silver electrode, and the silver electrode is converted into a silver-chloride electrode.

Yet another aspect of the invention is directed to a method of making an integrated circuit for a single-molecule nucleic-acid assay platform, comprising: forming a pair of electrodes on opposing ends of a carbon nanotube, the electrodes electrically connecting the carbon nanotube to a CMOS integrated circuit; and exposing the carbon nanotube to a diazonium salt solution to form a point defect on a portion of the carbon nanotube.

In one or more embodiments, the method further comprises applying a reaction liquid-gate bias voltage that promotes a reaction between (a) the diazonium salt solution and (b) the carbon nanotube to form the point defect. In one or more embodiments, the method further comprises applying an initial liquid-gate bias voltage to inhibit the reaction; and adjusting the liquid-gate bias voltage to the reaction liquid-gate bias voltage to promote the reaction. In one or more embodiments, the method further comprises monitoring an electrical current through the carbon nanotube while applying the reaction liquid-gate bias voltage; and detecting a discrete drop in the electrical current through the carbon nanotube; and returning the liquid-gate bias voltage to the initial liquid-gate bias voltage after detecting the discrete drop.

In one or more embodiments, the method further comprises applying the reaction liquid-gate bias voltage for a predetermined time period; and returning the liquid-gate bias voltage to the initial liquid-gate bias voltage at the end of the predetermined time period. In one or more embodiments, the method further comprises exposing the carbon nanotube to the diazonium salt solution for a predetermined time period; and rinsing the surface of the CMOS integrated circuit to halt a reaction between (a) the diazonium salt solution and (b) the carbon nanotube to form the point defect. In one or more embodiments, the method further comprises depositing a photoresist or an e-beam resist on a portion of the surface of the CMOS integrated circuit prior to exposing the carbon nanotube to the diazonium salt solution to define an isolated exposed region on the surface of the CMOS integrated circuit for a reaction between the carbon nanotube and the diazonium salt solution.

BRIEF DESCRIPTION OF THE DRAWINGS

For a fuller understanding of the nature and advantages of the present concepts, reference is made to the following detailed description of preferred embodiments and in connection with the accompanying drawings.

FIGS. 7A, 7B, and 7C are contour plots of the percentage of zero-nanotube, one-nanotube, and multiple-nanotube occurrences, respectively, for an electrode pair as a function of both nanotube density and electrode width.

DETAILED DESCRIPTION

An aspect of the disclosed subject matter provides systems and methods for single-molecule nucleic-acid assay platforms. Single-molecule nucleic-acid assay platforms according to the disclosed subject matter can provide improved sensitivity without amplification, while also providing improved multiplexing capabilities. Transduction can be performed label-free, which can simplify sample preparation protocols.

Another aspect of the disclosed subject matter relates to a spin-cast method for fabrication large arrays of metal-contacted single nanotubes. This method may be applied to the fabrication of passive array devices. The application of these techniques also includes but is not limited to fabrication of these devices within the back-end flow of a standard CMOS process. This is beneficial since the scope of smFET applications has been restricted by the low yield of fabrication. Large arrays of smFETs will enable parallelization and scale useful for many applications. The devices can be converted to smFETs by employing electrochemical reduction of compounds such as aryldiazonium salts. The reduction can be controlled with applied potential with yields for single defects of equal or better than 80%.

In accordance with certain embodiments, wafer-scale SWCNT-FET can be fabricated by covering the entire surface of a 100-mm silicon wafer with 285 nm of thermal oxide with 1-2 ml of a CNT suspension for spin coating (with a nanotube concentration of 1.6 to 2.5 μg/ml), resulting in a surface concentration of 0.13±0.02 CNTs/$\mu m^2$ post-spinning.

A method for controllably point functionalizing of these nanotube devices through a bias applied between the device and the surrounding electrolyte is also provided. In accordance with certain embodiments, the spin-cast devices may be exposed to 4-formylbenzene diazonium hexafluorophosphate (FBDP) with an applied liquid-gate potential ($V_{lg}$) to form an aryl point defect on a portion of the CNT. For example, at $V_{lg}$ of −500 mV, a m-SWCNT device exhibits a single current level with no discernible current drops for the entire recording time (515 seconds) after FBDP exposure.

In another embodiment, an m-SWCNT device with fixed $V_{lg}$ at 0 V exhibits discrete current levels 90-sec after FBDP exposure, which indicates the formation of a point defect on a portion of the m-SWCNT. At certain higher defect densities, transport can change from ballistic to localized with very significant increases in resistance. In some cases, m-SWCNT devices with higher initial resistance (>500 kΩ) can exhibit larger resistance steps during the FBDP incubation.

Figure 1:
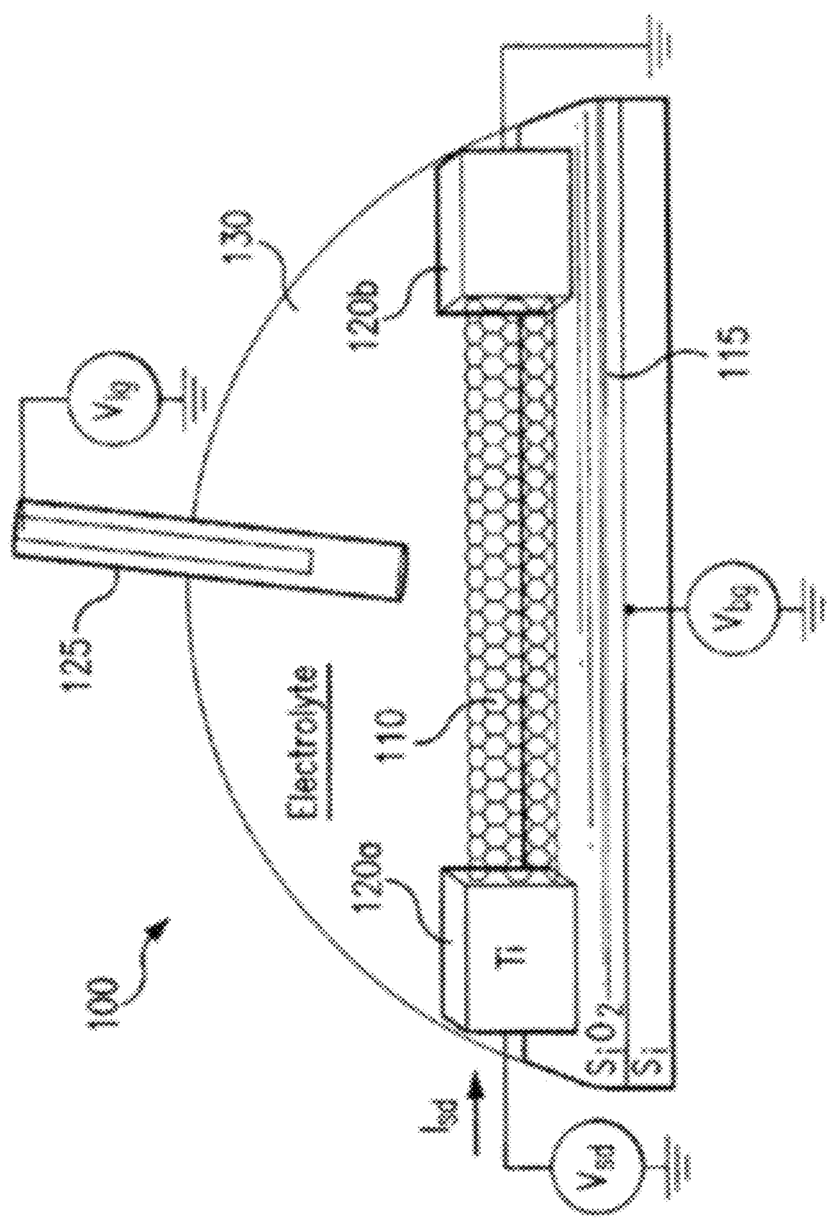
FIG. 1 is a diagram illustrating an exemplary embodiment of an assay platform according to the disclosed subject matter.

FIG. 1 is a diagram illustrating an exemplary nanoscale single-molecule field effect transistor (smFET) 100 according to the disclosed subject matter. A smFET 100, which can be utilized to perform transduction, can be configured as a carbon nanotube device 110 disposed on a substrate 115, which can be a silicon substrate and can have a silicon oxide layer disposed thereon. A capture probe, for example and as embodied herein, such as single-stranded DNA, can be immobilized onto the nanotube 110, and can be coupled to source electrode 120*a* and drain electrode 120*b*, each of which are embodied herein as titanium electrodes, and can be disposed at opposing ends of the nanotube 110. Alternatively, the source and drain electrodes 120*a*, 120*b* can comprise palladium, gold, platinum, silver, chromium, and/or aluminum. Additionally, source and drain electrodes 120*a*, 120*b* can be passivated with a photoresist or an e-beam resist. The smFET 100 can be configured to detect hybridization with a single target molecule at a relatively high signal-to-noise ratio, for example 3 or more, without labeling. As such, background or non-specific adsorption can be reduced.

Figure 2:
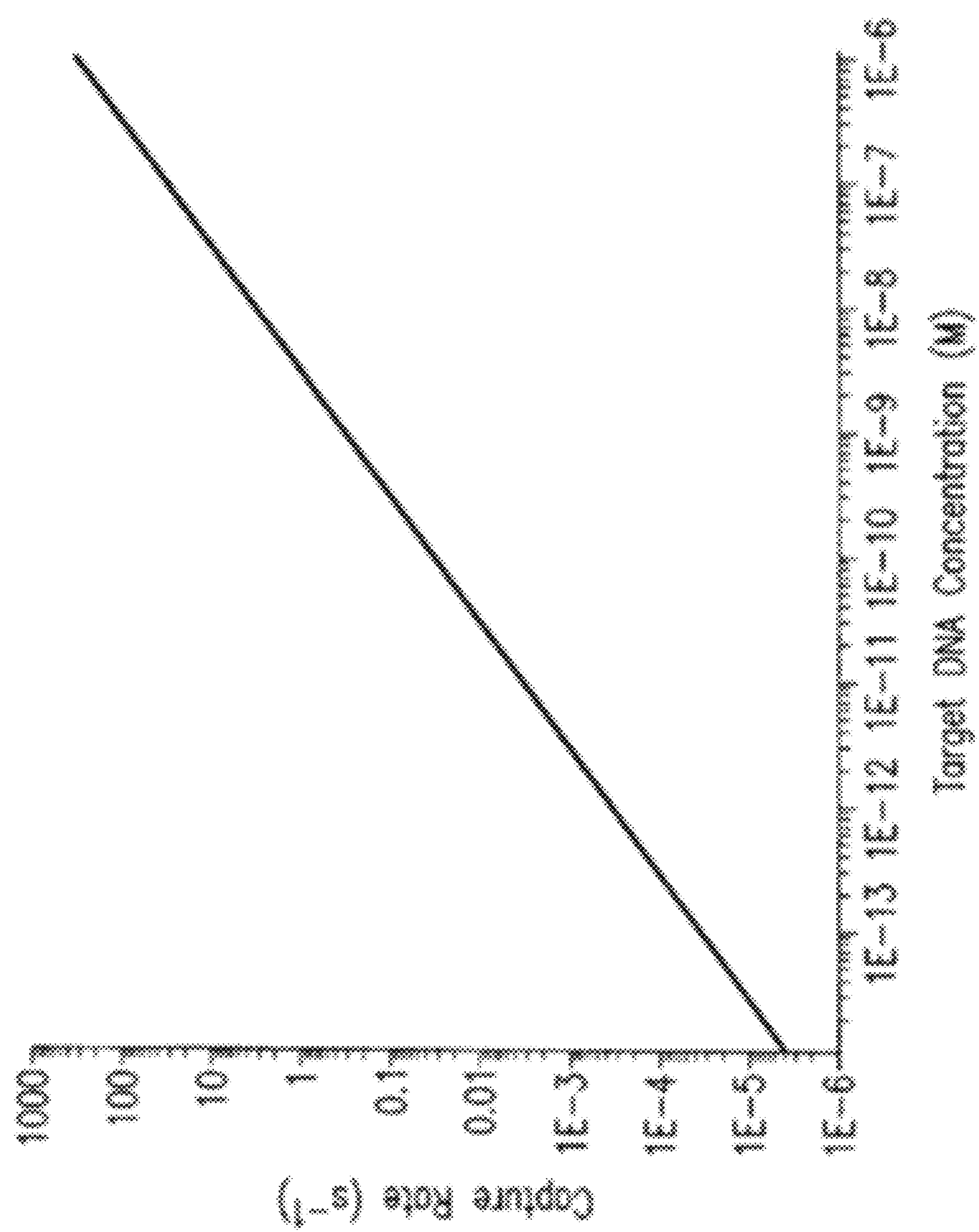
FIG. 2 is a diagram illustrating further details of the assay platform of FIG. 1.

The smFET 100 assay platform can operate differently from traditional ensemble assays. For example, and as embodied herein, rather than measuring the hybridization behavior of an ensemble, as in a traditional microarrays, the smFET 100 assay platform can measure the time between capture events. Capture rates can thus be diffusion limited and concentration dependent. As such, low levels of detection, as low as one molecule, can be performed, which can be affected at least in part by diffusion time of the target to the sensor site. With reference to FIG. 1, the diffusion time can be reduced with a bias applied between the nanotube 110 and a reference electrode 125, for example and embodied herein as an Ag/AgCl (e.g., silver chloride) electrode or platinum electrode, in the electrolyte 130 that surrounds it, and the bias can be referred to as a liquid gate bias $V_{lg}$. In another example, the reference electrode 125 comprises platinum, palladium, and/or silver. FIG. 2 is a diagram illustrating the estimated capture rate for 33-mer ssDNA, with a 300 mV bias applied, as a function of target concentration. Furthermore, the capture rate can be independent of the size of the target DNA being captured. Additionally or alternatively, and as described further below, the carrier density in the nanotube 110 can be controlled through a global back gate $V_{bg}$ applied through the substrate 115.

Nanotube and nanowire field-effect sensors can be utilized as biosensors. In some implementations, an electrolyte buffer with mobile ions can be used to gate the transistor. The sensing mechanism can be attributed at least in part to changes in the Schottky barrier at the contacts and electrostatic doping of the nanotube channel due to adsorption of biomolecules.

As embodied herein, introducing a defect onto the nanotube 110 surface can provide smFET 100 sensors with localized charge sensitivity and improved gain. Such defects can, in turn, be used to covalently bind molecules at the scattering site. The resulting smFET 100 device can have improved sensitivity and detect the binding of a single molecule, due at least in part to Coulomb interactions between the molecule and the defect which modulates scattering in the 1D channel. The charge sensitivity can be screened by counterions and can be localized to the region of the defect. The single-point defects can be electrochemically created in a controllable manner, as described in further herein. Such defect-dominated conductance in nanotubes can produce measurements of DNA hybridization kinetics with suitable high signal-to-noise ratio (SNR) and bandwidth to measure single-molecule kinetics and thermodynamics through a label-free smFET approach.

Figure 3:
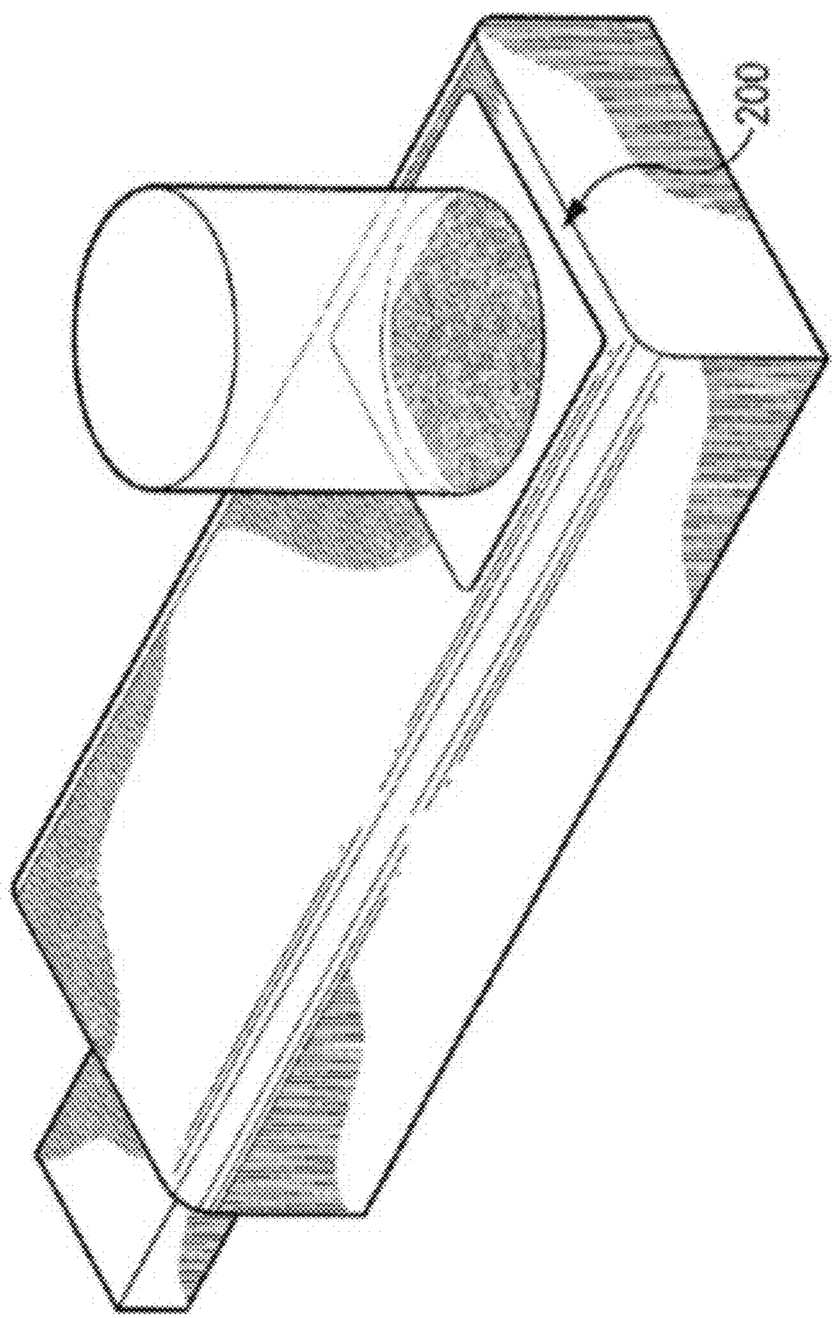
FIG. 3 is a diagram illustrating the assay platform of FIG. 1 configured on a form factor of a USB stick.
Figure 4A:
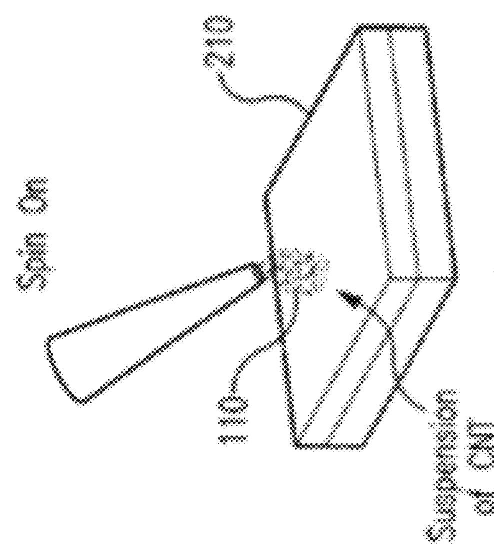
FIGS. 4A, 4B, and 4C are diagrams illustrating exemplary techniques for transferring nanotubes onto an integrated circuit substrate.

According to another aspect of the disclosed subject matter, an integrated circuit for a single-molecule nucleic-acid assay platform is provided. With reference to FIGS. 3-5, in an exemplary embodiment, an assay platform 200 can include one or more of smFETs 100 disposed on a complementary metal-oxide semiconductor (CMOS) integrated circuit 210. The assay platform 200 can allow for the development of an assay device configured on a form factor of a USB stick, as shown for example in FIG. 3. The integrated circuit 210 can be configured, for example and without limitation, with dimensions from 1 mm to 20 mm on each side, and as embodied herein as a 5-mm-by-5-mm integrated circuit chip fabricated in an IBM 0.13-μm CMOS technology. Integrated circuit 210 can include, for example and without limitation, 10 to 1,000 measurement channels each multiplexed to 100 to 1,000 smFET devices per channel, and as embodied herein having 12 measurement channels each multiplexed to 500 smFET devices per channel. Platform 200, in addition to improved integration, can allow for improved fabrication of these nanotube devices.

Various techniques can be utilized to transfer one or more nanotubes 110 to a substrate of a CMOS integrated circuit 210. FIG. 4A illustrates an exemplary technique for transferring nanotubes 110 to a substrate of CMOS integrated circuit 210. The technique of FIG. 4A involves spinning-coating the surface of the CMOS integrated circuit 210*a* with a suspension of carbon nanotubes, for example similar to spinning on a photoresist.

Figure 4B:
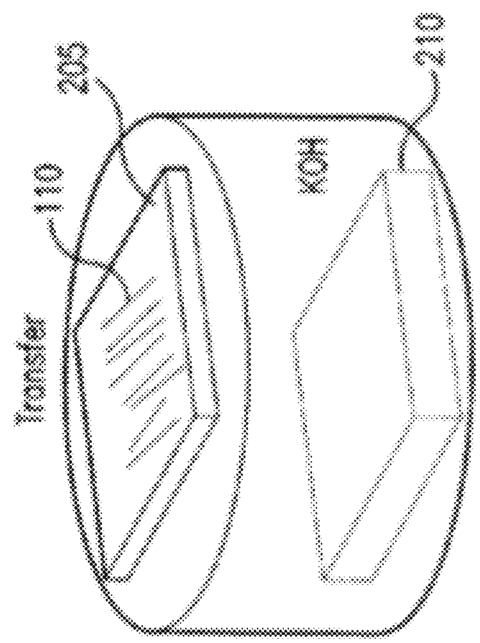
Figure 5:
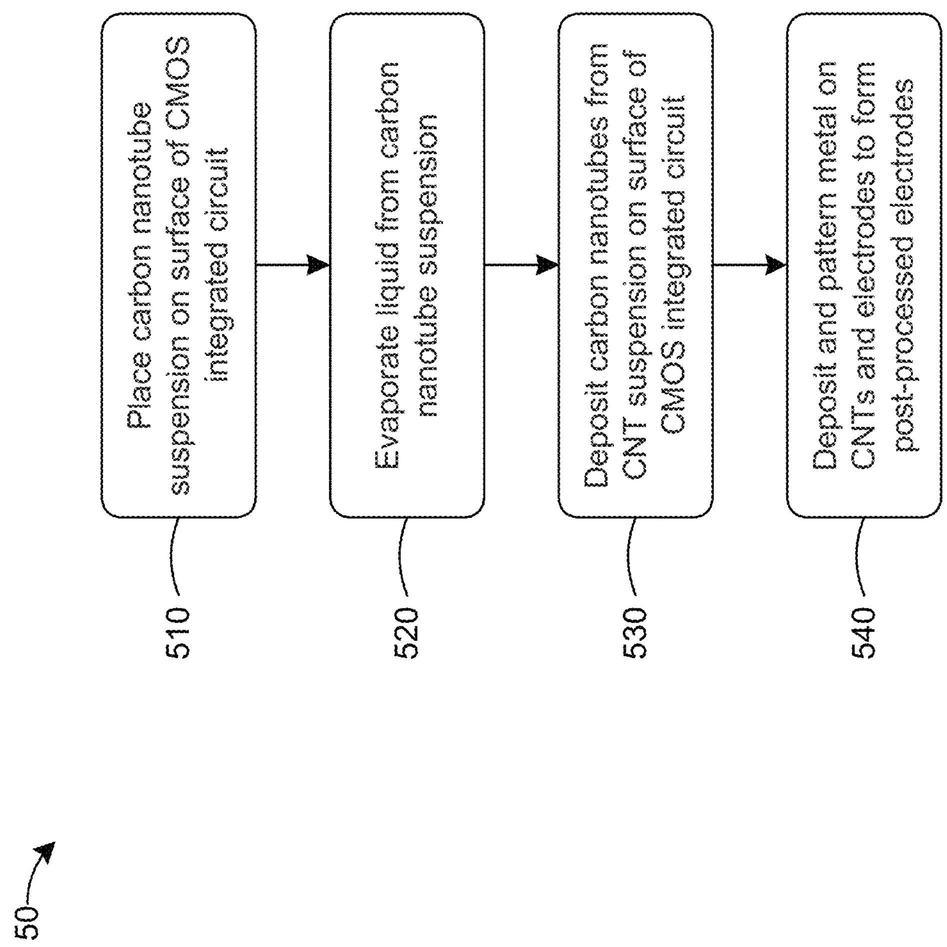
FIG. 5 is a flow chart of a method of making an integrated circuit for a single-molecule nucleic-acid assay platform using a carbon nanotube suspension.

Alternatively, as illustrated in FIG. 4B, nanotubes 110 can be transferred by growing carbon nanotubes 110 on a surface of a growth substrate (e.g., a quartz substrate) and then spinning on a thin film polymer 205 (for example, embodied herein as polymethyl methacrylate) that can lift off in strong bases (for example, potassium hydroxide or sodium hydroxide) with the nanotubes 110 attached or adhered to a surface of the thin film polymer 205. The thin film polymer 205 can have a thickness of about 50 nm to about 1,000 nm, including about 250 nm, about 500 nm, about 750 nm, or any thickness or thickness range between any two of the foregoing thicknesses. The surface of the thin film polymer 205 with the nanotubes 110 attached thereto can then be placed on top of the CMOS substrate 210, along with the nanotubes 110. As such, the density of nanotubes 110 can be adjusted through the growth recipe of the carbon nanotubes 110. Furthermore, using quartz substrates can improve density and alignment of the nanotube 110 arrays, which can be suitable for biosensors.

After the thin-film polymer 205 is placed on top of the CMOS substrate 210, along with the nanotubes 110, the thin-film polymer 205 is chemically removed, for example by soaking the CMOS substrate 210 in acetone (and/or another organic solvent). The CMOS substrate 210 can be subsequently rinsed in isopropanol and dried using nitrogen. Subsequently, the CMOS substrate 210 can undergo a high-temperature anneal to remove any residual polymer. The anneal can occur in vacuum, in nitrogen, in forming gas, in argon, under oxygen, or in air. Chemically removing the thin film polymer 205 causes the nanotubes 110 to be released from the thin-film polymer 205 and deposited onto the surface of the CMOS substrate 210.

Alternatively, a thin film of gold can be used to transfer nanotubes 110 to the CMOS substrate 210. For example, gold film (e.g., a high purity gold film) can be deposited onto the solid substrate and the nanotubes 110 attach or adhere to a first surface of the thin gold film. The gold film, which can be preferably about 50 nm thick or greater, can be deposited by physical vapor deposition or electroplating. After the gold film is deposited, it is mechanically pulled off of the solid substrate. Tape or a polymer (e.g., polydimethylsiloxane (PDMS)) can be applied to the second surface of the gold film to provide a handle for peeling off the gold film from the solid substrate. The nanotubes 110 that are attached or adhered to the first surface of the gold film are pulled off of the solid substrate when the gold film is peeled off of the solid substrate. The first surface of the gold film with the nanotubes 110 attached thereto is then placed on top of the CMOS substrate 210, along with the nanotubes 110. After the gold film is placed on top of the CMOS substrate 210, along with the nanotubes 110, the gold film is chemically removed by wet etching. Chemically removing the gold film causes the nanotubes 110 to be released from the gold film and deposited onto the surface of the CMOS substrate 210.

Figure 4C:
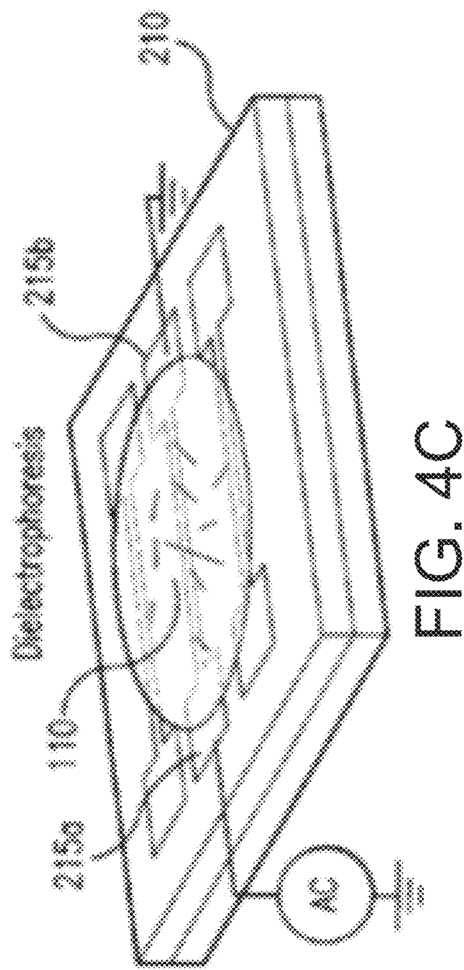

FIG. 4C illustrates another exemplary technique for transferring nanotubes 110 using dielectrophoresis. In this technique, by applying an AC voltage between electrodes 215*a*, 215*b*, a force can be applied to nanotubes 110 proportional to the gradient of electric fields. The CMOS chip 210 can aid in applying the field and stop the field when a nanotube 110 has bridged the electrodes. In each of the above transfer techniques, an active CMOS chip 210 with a dense electrode array, for example having 1,000 or more electrode pairs per $mm^2$, can be used to locate where a nanotube bridges two contacts, and in this manner can guide the location of the nanotubes 110.

In one or more alternative embodiments, the carbon nanotubes are disposed in a carbon nanotube suspension. FIG. 5 is a flow chart 50 of a method of making an integrated circuit for a single-molecule nucleic-acid assay platform using a carbon nanotube suspension.

In step 510 a carbon nanotube suspension is placed on the surface of the CMOS integrated circuit. The CMOS integrated circuit includes source and drain electrodes 600A, 600B (FIG. 6) that are electrically coupled to internal electronics within the CMOS integrated circuit 210. In some embodiments, the source and drain electrodes 600A, 600B can be formed out of metal such as titanium, palladium, gold, platinum, silver, chromium, and/or aluminum.

The carbon nanotube suspension includes carbon nanotubes suspended in a liquid. The liquid can be water that includes surfactants, which can help keep the nanotubes well-dispersed. The surfactants can include sodium dodecyl sulfate, sodium cholate, cetyl trimethyl ammonium bromide, polyoxyethylene (20) sorbitan monolaurate (e.g., TWEEN® 20 available from Sigma-Aldrich, Inc.), 4-(1,1,3,3-tetramethylbutyl)phenyl-polyethylene glycol (e.g., TRITON™ X-100 available from Sigma-Aldrich, Inc.), and/or sodium deoxycholate. Alternatively, the liquid can include an organic solvent such as toluene. For example, in the case of toluene, the liquid can include one or more polymers (e.g., the copolymer of 9,9-dioctylfluorenyl-2,7-diyl and bipyridine (PFO-BPy)) that help keep the nanotubes well-dispersed. The liquid can also be an organic solvent that does not require any surfactants or polymers to help keep the nanotubes well-dispersed, such as N-methyl-2-pyrrolidone (NMP), N-cyclohexyl-2-pyrrolidone (CHP), and/or dimethylformamide (DMF).

A variety of techniques can be used to place the carbon nanotube suspension on the surface of the CMOS integrated circuit such as spin-coating or spraying (e.g., using a spray nozzle, a printer head nozzle (e.g., in an ink jet or 3D printer), or an ultrasonic nozzle). Spraying can occur in a rasterized manner to improve the uniformity of the thickness and distribution of the carbon nanotube suspension across the surface of the CMOS integrated circuit. The spraying process may occur in air or in an inert atmosphere (nitrogen or argon) to prevent the solvent/liquid from undergoing any sort of reaction with oxygen at elevated temperatures (e.g., during step 520).

In step 520, the liquid (e.g., water or organic solvent) in the carbon nanotube suspension is evaporated. For example, the evaporation can occur as a result of the spin-coating deposition process without additional heating. The evaporation can occur during or after the spay deposition process. For example, heating and evaporation can occur in the spray deposition process itself and/or during the spray deposition process by placing the substrate on a hot plate. Heating can also occur after the spray deposition process in an oven, on a hot plate, or by another process. In some embodiments, the CMOS integrated circuit can be heated to within a temperature range of about 40° C. up to about 250° C. to promote substantially complete evaporation of the liquid (e.g., solution or solvent) in the carbon nanotube suspension. As used herein, "about" means plus or minus 10% of the relevant value.

The heat can cause the liquid to evaporate when (or approximately when) the carbon nanotube suspension touches the surface of the CMOS integrated circuit 210 to deposit the carbon nanotubes thereon in step 530 without re-aggregating the carbon nanotubes on the surface of the CMOS integrated circuit 210. The carbon nanotubes can have a continuous uniform probability distribution across the surface of the CMOS integrated circuit. In step 540, a metal is deposited and patterned onto the CMOS integrated circuit to form post-processed contacts/electrodes 220. The post-processed contacts 220 form an electrical connection between the carbon nanotube(s) and the source and drain electrodes 600A, 600B of the CMOS integrated circuit. The metal can include titanium, palladium, gold, platinum, silver, chromium, and/or aluminum.

Previous spin-cast efforts have utilized multiple deposition cycles to manipulate the thin-film deposition of unbundled nanotubes from an air-liquid interface or laminar flow at a liquid-liquid interface. Deposition conditions can be affected by multiple parameters, such as flow velocity, surface pressure, and/or thin-film thickness, and it can make the manufacturing process difficult. Using a single spin cycle (e.g., in step 510) to randomly place a dilute SWCNT suspension across large wafer surfaces reduces or eliminates one or more of these manufacturing problems. For example, using a single spin cycle results in the evaporation of the solvent in the SWCNT suspension without any additional heating (e.g., in subsequent processing steps).

Simulations enable understanding of the relationship between spin-cast parameters and device yield. In one embodiment, the expected number of nanotubes bridging on the fixed electrode pairs is a function of both nanotube density and electrode width (w) at a fixed electrode gap (I) of 0.5 μm (spacing between electrodes) and an electrode height (h) of 10 μm. The nanotube solution used can comprise a purified, commercially-available unsorted SWCNT solution (e.g., <5% carbonaceous impurities). The electrodes can be designed as a zig-zag shape to allow for CNT transits in both the horizontal and vertical directions. In the simulations, placement of nanotubes by spin-cast deposition is assumed to produce a continuous uniform probability distribution across the wafer.

Both higher nanotube density and wider electrodes are expected to result in a higher frequency of nanotube bridges between electrode pairs. In this embodiment, statistics are collected for 500 simulated electrode pairs with a nanotube density ranging from 0.05 CNT/$\mu m^2$ to 0.25 CNT/$\mu m^2$ and electrode widths ranging between 5 μm and 25 μm. FIGS. 7A-C are contour plots of the percentage of zero-nanotube, one-nanotube, and multiple-nanotube occurrences, respectively, for an electrode pair as a function of both nanotube density and electrode width. The probability of precisely incorporating a single nanotube between a 20-μm-wide electrode pair in this embodiment is slightly higher than 30% for nanotube densities between 0.15 and 0.20 CNTs/$\mu m^2$. The theoretical maximum yield of single CNT crossings, dictated by Poisson statistics, is approximately 36% (P(I)=I/e). The probability of incorporating multiple nanotubes between a 20-μm-wide electrode pair in this embodiment is about 15% for nanotube densities between 0.15 and 0.20 CNTs/$\mu m^2$.

Figure 6:
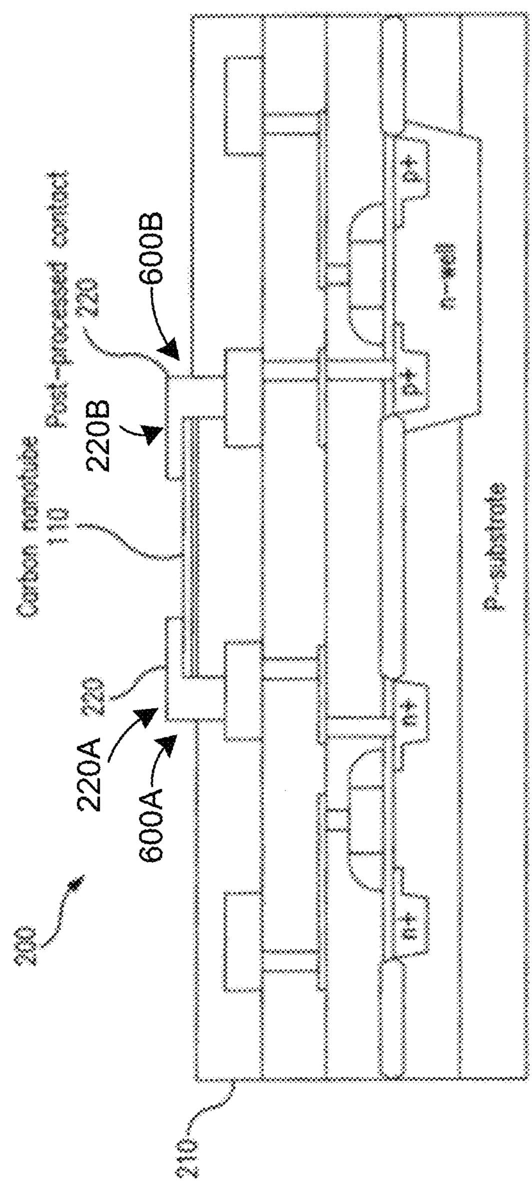
FIG. 6 is a diagram illustrating an exemplary embodiment of an integrated circuit and nanotube for a single-molecule nucleic-acid assay platform.
Figure 8B:
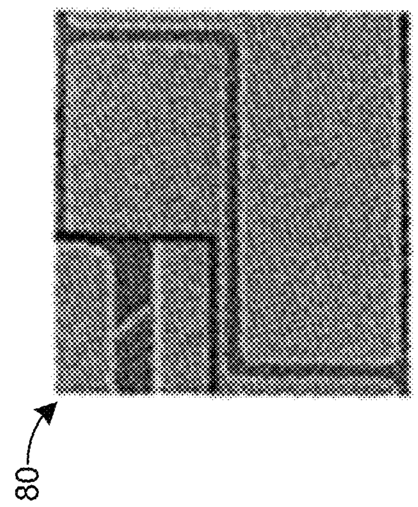
FIGS. 8A, 8B, 8C, and 8D are representative micrographs of devices with single nanotube crossings, taken at various locations on a single die.
Figure 8D:
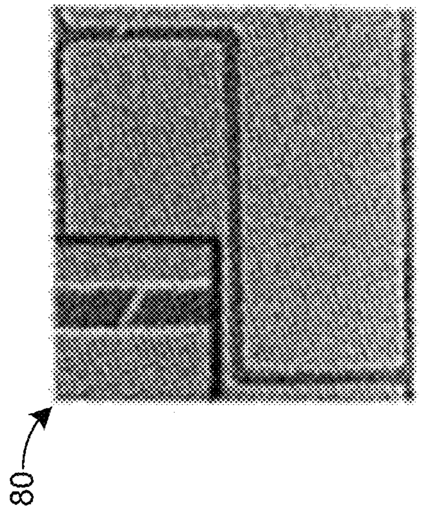
Figure 8A:
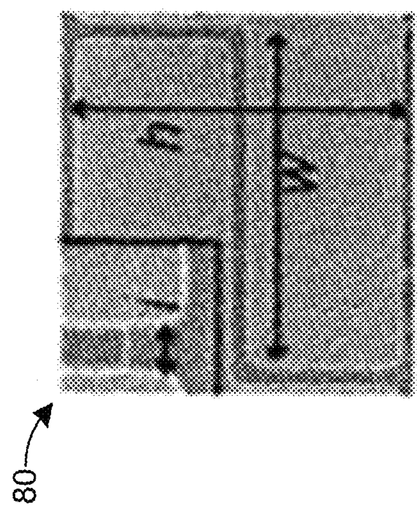
Figure 8C:
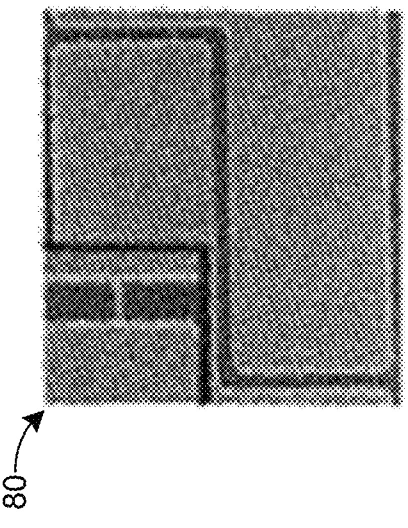

After transfer of nanotubes 110 to the substrate of the CMOS integrated circuit 210, additional lithography and metallization can be performed to deposit a metal, such as titanium, palladium, gold, platinum, silver, chromium, and/or aluminum to form post-processed electrodes 220A, 220B connecting the nanotubes 110 to the integrated circuit 210, as shown for example in FIG. 6. The metal can be deposited onto exposed aluminum electrodes on substrate 215, or alternatively, the exposed aluminum electrodes can be etched away and replaced with titanium, palladium, gold, platinum, silver, and/or chromium. Additionally, a further set of surface-exposed aluminum electrodes can be etched away and replaced with a reference electrode. The integrated reference electrodes allow control of the electrolytic potential gating the nanotube sensors.

The reference electrodes can be formed, for example and without limitation, by electroplating silver with subsequent chlorination with $FeCl_3$. The reference electrodes can thus be configured as Ag/AgCl electrodes, which can have a relatively low current level therethrough, and thus can operate for days continuously before being exhausted. Chlorination of the Ag/AgCl electrodes can be repeated multiple times before the silver electrode can become exhausted at which point it can be re-electroplated. Additionally or alternatively, platinum can be deposited to create the reference electrodes to allow control of the electrolytic potential gating the nanotube 110. Platinum can be deposited onto the set of surface-exposed aluminum electrodes, or the set of surface-exposed aluminum electrodes can be etched away and replaced with platinum. Additionally or alternatively, palladium can be deposited to create the reference electrodes to allow control of the electrolytic potential gating the nanotube 110. Palladium can be deposited onto the set of surface-exposed aluminum electrodes, or the set of surface-exposed aluminum electrodes can be etched away and replaced with palladium. Thus, the reference electrodes can comprise platinum, palladium, and/or or silver. Additionally or alternatively, one or more external reference electrodes 125 can be utilized to allow control of the electrolytic gating potential, as described herein. The external reference electrodes 125 can be formed of the same material(s) and/or different material(s) than reference electrodes.

Integration of nanotubes 110 with CMOS chips 210 can allow multiple devices to be integrated on the same measurement substrate and can allow reduction in the parasitic capacitance associated with assay measurements. As such, measurement bandwidth can be increased while reducing amplifier noise. Furthermore, the integrated circuit 210 CMOS substrates can also be automated to quickly probe devices and select those with suitable performance.

Concentrations of target analytes can be determined by the mean time between capture events, as shown for example in FIG. 2. Concentrations as low as 100 fM can be detectable within approximately 8 hours. The assays can be performed at a temperature such that after capture, there is suitable thermal energy, which can be based at least in part on the size of the target and the buffer concentration, for the captured molecule to escape again and allow for a new capture event. After a capture event, the molecule can again be recaptured. The detailed kinetics of these multiple capture events can provide additional information to identify single-nucleotide polymorphisms (SNPs) and other partial mismatches. By contrast, in certain microarrays, concentration and mismatch affinity cannot be independently determined.

The capture probe can be immobilized or programmed on a site-specific basis, for example and as embodied herein through either robotic spotting or through electrically programmed immobilization. With robotic spotting, drops of capture probe can be placed over each selected site. In this manner, sensor density can have a pitch as low as approximately 150-μm. With electrically programmed immobilization, individual probe sites can be electrically selected such that only those selected sites can bind the probe. In this manner, sensor density can be increased without limit over that obtained with robotic spotting.

Example 1

In a specific example, about 1 ml to about 2 ml of a CNT suspension (with a nanotube concentration of about 1.6 μg/ml to about 2.5 μg/ml) was spin-coated onto a thermal oxide layer on a 100-mm silicon wafer using a single spin cycle during which the liquid in the CNT suspension is evaporated. The thermal oxide layer can be about 285 nm thick, and the resulting surface concentration is 0.13±0.02 CNTs/$\mu m^2$, assessed from eleven SEM micrographs (with the field of view of 500 $\mu m^2$) of the wafer post-spinning.

Metal electrodes were then deposited on top of the carbon nanotubes through a photolithographic process. The metal extended out to the side of the chip, where it was electrically connected to a measurement board through wire bonds.

Each wafer prepared this way yielded 45 chips (11-mm-by-10-mm size); each chip contained 280 pairs of source-drain electrical contacts (w=20 μm, I=0.5 μm, and h=10 μm). Representative micrographs of devices with single nanotube crossings, taken at various locations on a single die, are shown in FIGS. 8A-D. An inset 80 in each figure show a more magnified view of the nanotube crossing.

Figure 9:
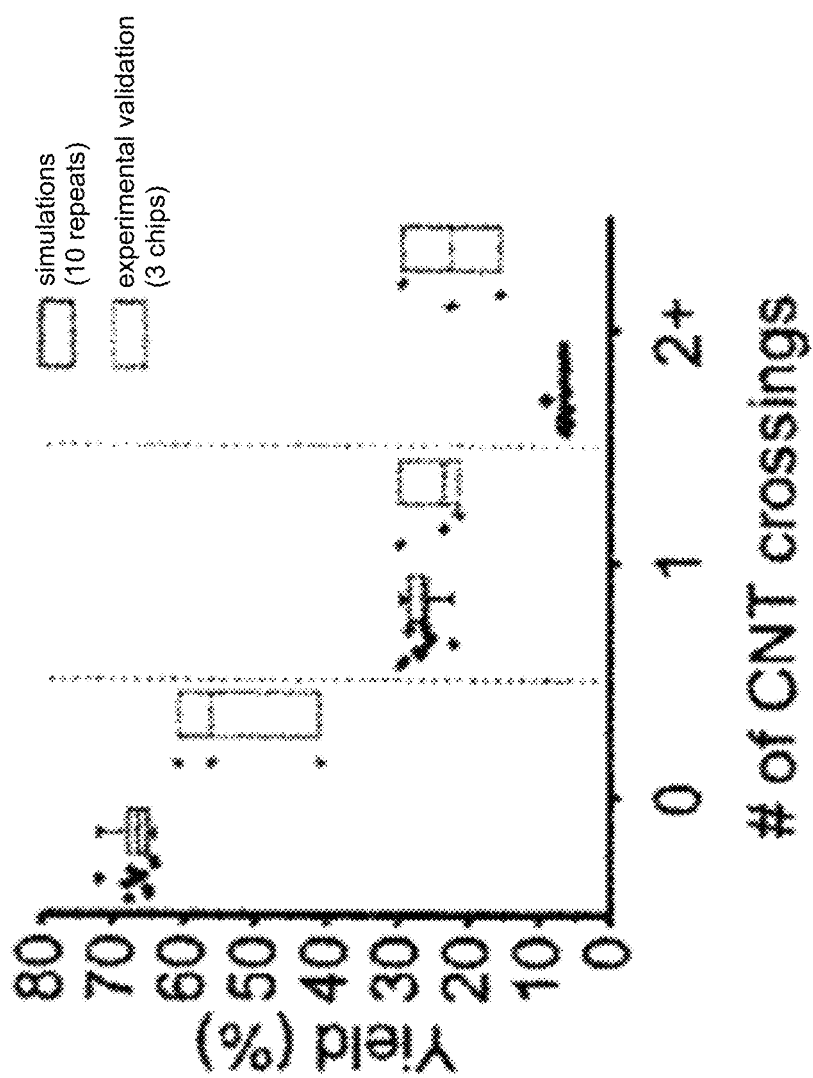
FIG. 9 illustrates a statistical comparison of simulated and experimental yields for spin-cast nanotubes.

FIG. 9 illustrates a statistical comparison of simulated and experimental yields for spin-cast nanotubes. Simulations predict an average yield of zero-crossings of 65%, single-crossings of 27%, and multiple crossings of 8% for the same CNT surface concentration (0.13 CNTs/$\mu m^2$) and electrode width employed in these experiments (20 μm), compared with experimentally-measured values of 53%, 25%, and 22%, respectively. The experimental single-crossing yield, an important criterion for smFET fabrication, matches closely with simulation results. Nanotube bundling is not accounted for in these simulations.

Figure 10B:
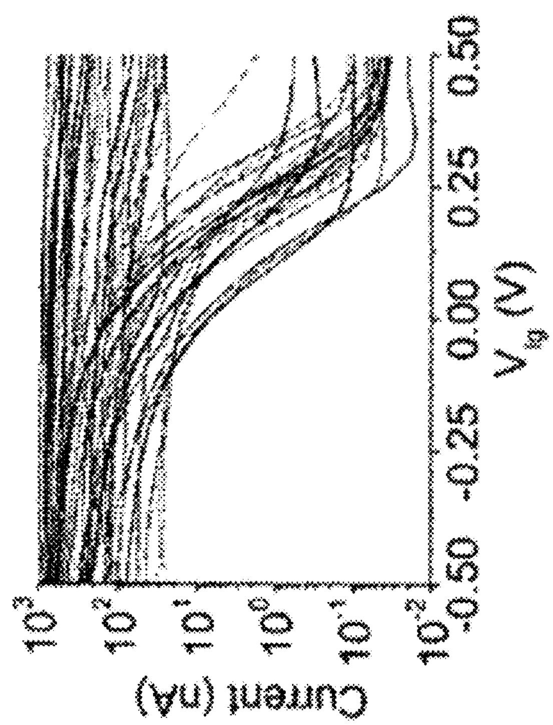
FIG. 10B illustrates the current as a function of the liquid-gate potential for devices that include single nanotube crossings.
Figure 10A:
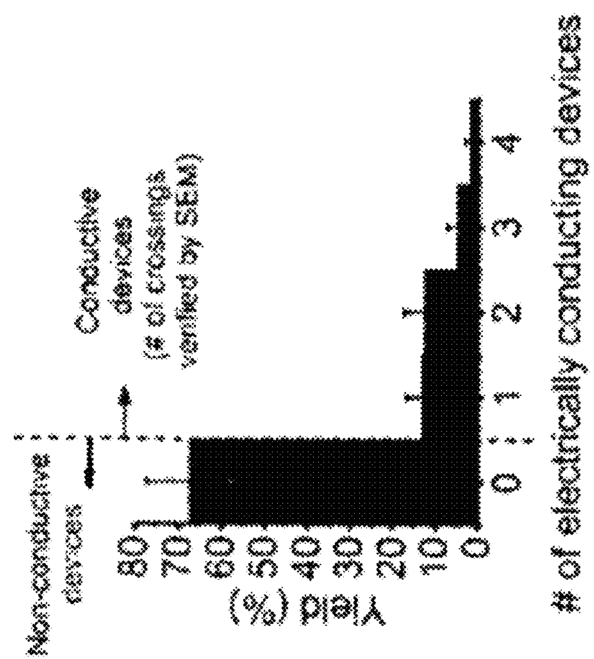
FIG. 10A is a histogram of the percentage yield as a function of the number nanotube crossings.

To ensure that the SWCNT devices electrically conduct after all processing steps, current-voltage (I-V) characteristics of 1,960 electrode pairs from seven chips were examined by applying back-gated voltage sweeps ($V_{bg}$, applied on the underlying silicon substrate) from −10 to +10 V. Since solution-processed SWCNTs are composed of mixtures of metallic (m-SWCNTs) and p-type semiconducting nanotubes (s-SWCNTS), conductive devices were determined based on measured on-current ($I_{on}$) at $V_{bg}$=−10 V and a source-to-drain ($V_{sd}$) of 100 mV. Conductive SWCNTs were defined by an $I_{on}$ of at least 1.0 nA, and 67.4±9.9% of electrode pairs were identified as non-conductive, as illustrated in FIG. 10A. The remaining conducting devices were subsequently investigated with scanning electron microscopy (SEM). As a result, 13.1±3.9% of the total electrodes shows both single and conducting nanotube bridges, corresponding to approximately 36 devices per chip. This yield is lower than the yield from SEM inspection alone (25%) because a CNT bridging an electrode pair can be imperfectly contacted, which is difficult to detect in an SEM image.

After initial electrical characterization, several chips containing tens of working SWCNT devices were wire-bonded to land-grid array (LGA) packages to interface with a custom printed circuit board. Once a microfluidic chamber was attached to the chip surface, aqueous buffer solution (e.g., 100 mM sodium phosphate buffer at pH 8.0) was introduced. I-V characteristics were measured by varying $V_{lg}$, set by a Pt electrode relative to the source potential of the device, as illustrated in FIG. 10B. These devices not only have a single CNT bridge but also exceed threshold $I_{on}$ values of 1 nA in I-$V_{lg}$ characteristics at $V_{sd}$=100 mV. Both semiconducting and metallic electrical behavior is evident. The peak current levels (between 10 nA and 1000 nA) for spin-cast devices are comparable to those previously reported for CVD-grown carbon nanotube devices with similar CNT length. Much of the observed variance in the conductance is attributed to variance in tube diameters and chirality. m-SWCNT are preferred for these studies because devices showing measurable conductance over the wide $V_{lg}$ range allow for more detailed application of electronic melting as well as the optimization of gate-dependent SNR.

Figure 11:
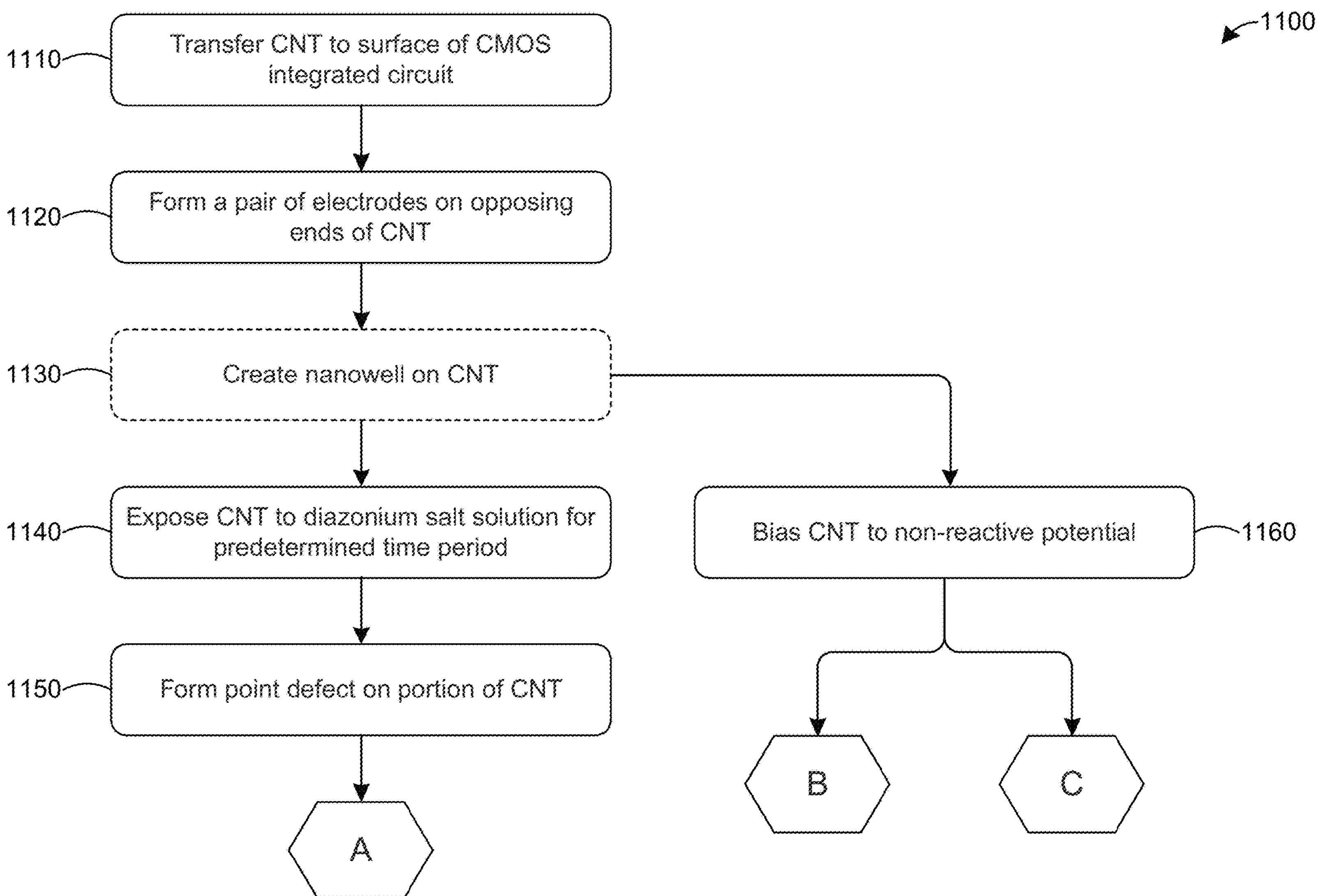
FIG. 11 is a flow chart of a method for making an integrated circuit for a single-molecule nucleic-acid assay platform that includes a point defect according to one or more embodiments.
Figure 11:
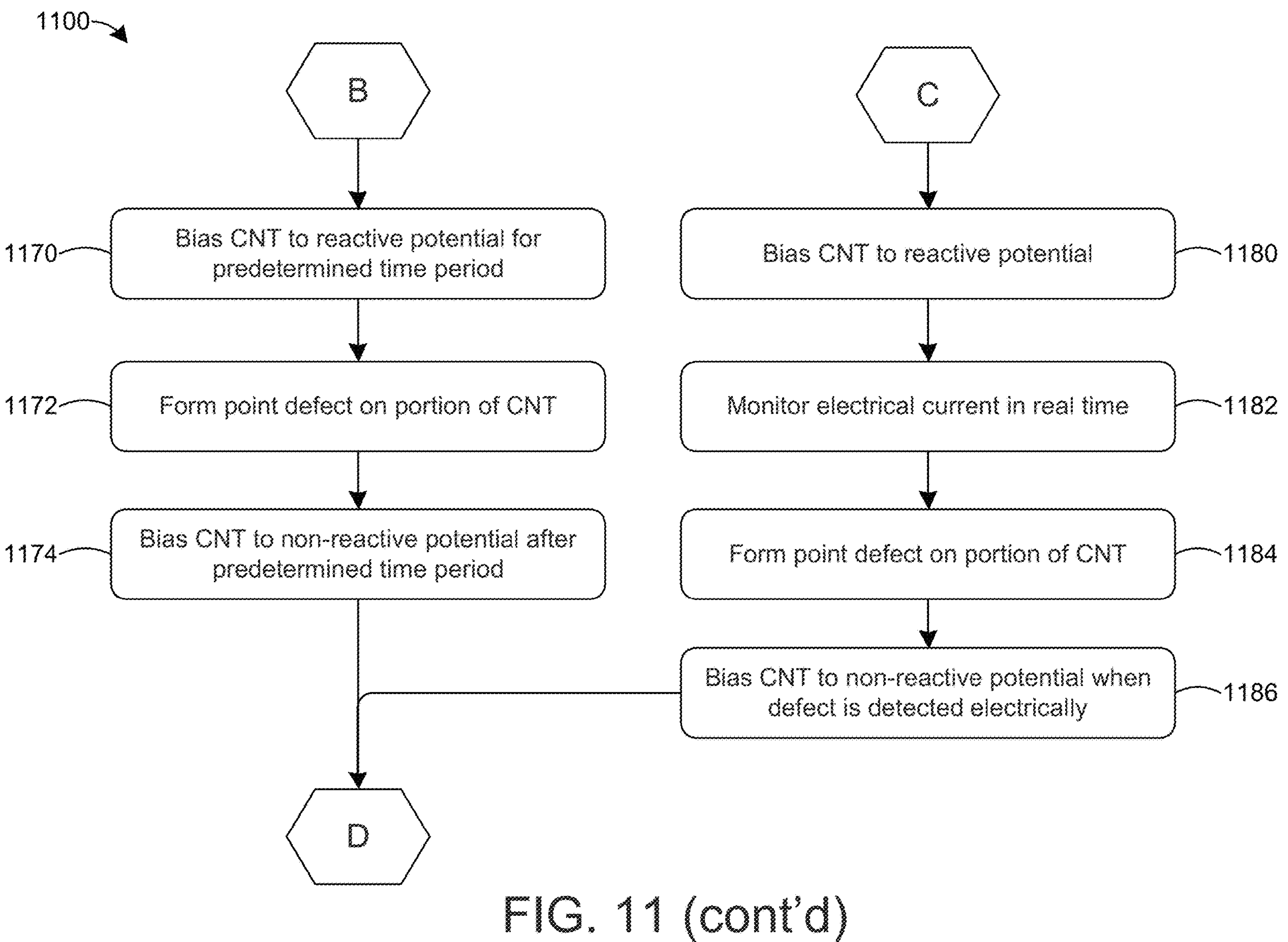
Figure 11:
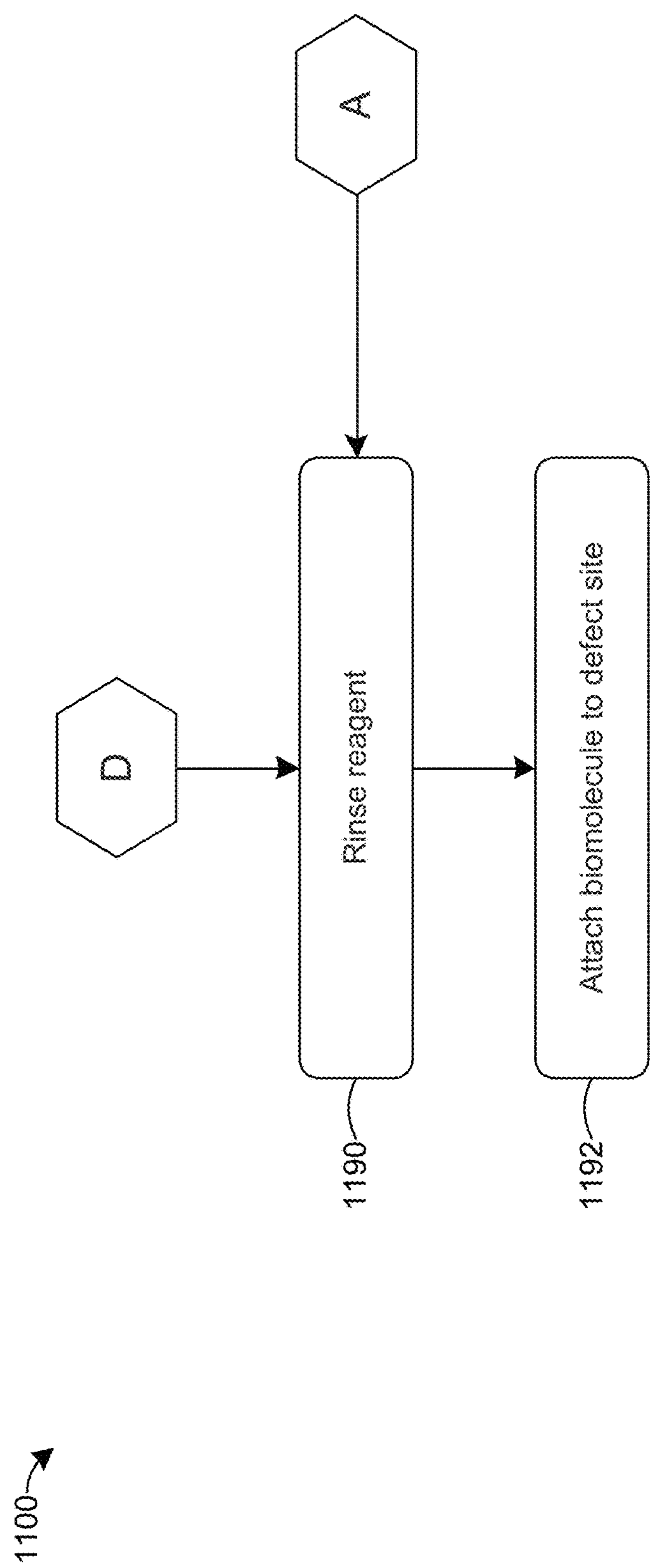

As discussed above, it can be advantageous to create a functionalized point or a functionalized point defect in or on the carbon nanotube to improve the sensitivity of the device (e.g., by reducing the region of charge sensitivity to the region around the functionalized point or functionalized point defect). FIG. 11 is a flow chart 1100 of a method for making an integrated circuit for a single-molecule nucleic-acid assay platform that includes a point defect according to one or more embodiments. In step 1110, a CNT (or CNTs) is transferred to a surface of a CMOS integrated circuit according to one of the methods described herein. For example, the CNT(s) can be transferred by using a gold or a polymer film as discussed above. In another example, the CNT(s) can be transferred by spin-coating a CNT suspension on the CMOS integrated circuit.

In step 1120, a pair (or pairs) of electrodes is formed on the surface of the CMOS integrated circuit such that each electrode is electrically coupled to opposing ends of the CNT. The pair of electrodes can include a source electrode and a drain electrode which can be the same as source electrodes 120*a*, 320*a* and drain electrodes 120*b*, 320*b*, respectively. The electrodes can be formed before or after the CNT(s) is/are transferred to the CMOS integrated circuit. For example, the electrodes can be formed before the CNT(s) is/are transferred to the CMOS integrated circuit when CNTs are transferred using dielectrophoresis (e.g., using an AC signal for nanotube placement). In other embodiments, the source and drain electrodes are formed and then, after the CNTs are transferred to the CMOS integrated circuit, a metal (e.g., titanium, palladium, gold, platinum, silver, chromium, and/or aluminum) is deposited and patterned to form electrical bridges (e.g., post-processed contacts or electrodes 220) between one or more CNTs and the source and drain electrodes.

In optional step 1130, one or more nano-wells is/are created on each CNT. The nano-well(s) can be created by depositing and patterning a photoresist or an e-beam resist (e.g., PMMA (poly(methyl methacrylate)) on the CMOS integrated circuit surface. The resist can be patterned and developed to define the nano-wells in the gaps between the resist. The nano-well(s) define discrete area(s) (e.g., reaction area(s)) on the CMOS integrated circuit surface, including on the CNT(s), where the diazonium salt solution can contact the CNT(s). The CMOS integrated circuit surface on which the resist remains is not exposed (or is not substantially exposed such that a reaction will occur) to the diazonium salt solution.

After optional step 1130, flow chart 1100 proceeds to either step 1140 or step 1160.

In step 1140, the CNT(s) is/are exposed to the diazonium salt solution for a predetermined time period (e.g., 90 seconds to 24 hours depending on the concentration of the diazonium salt solution). An example of a diazonium salt solution is 4-formylbenzene diazonium hexafluorophosphate (FBDP), which forms an aldehyde group as the point defect on the CNT.

In step 1150, a point defect is formed on a portion of the CNT. For example, the point defect can include an aldehyde group, as discussed above. After step 1150, flow chart 1100 proceeds to step 1190 (discussed below) via placeholder A.

In step 1160, which follows optional step 1130, a liquid-gate bias voltage $V_{lg}$ is applied to the CNT at a potential that inhibits the reaction between (a) the diazonium salt solution and (b) the CNT. For example, the bias voltage $V_{lg}$ can be initially set at −500 mV or lower to inhibit the reaction in step 1160.

Figure 12A:
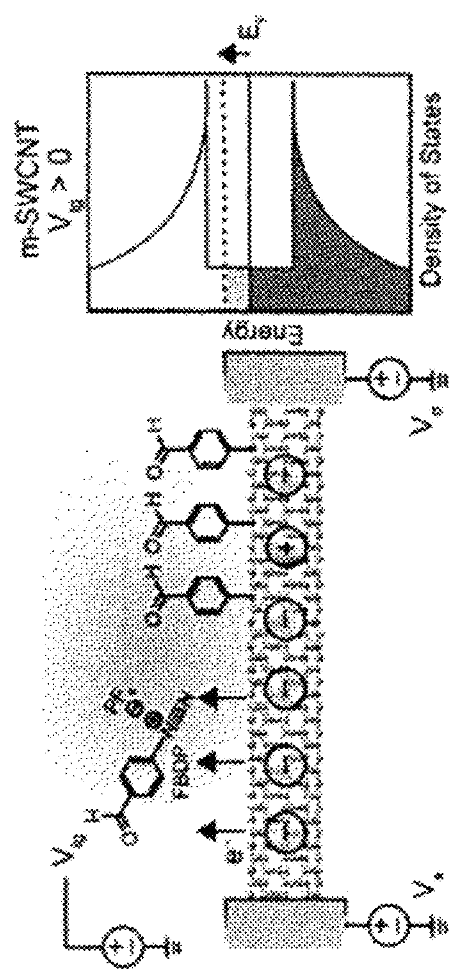
FIG. 12A illustrates a liquid-gate-potential-dependent diazonium reaction bias voltage when the liquid gate potential is positive.
Figure 12B:
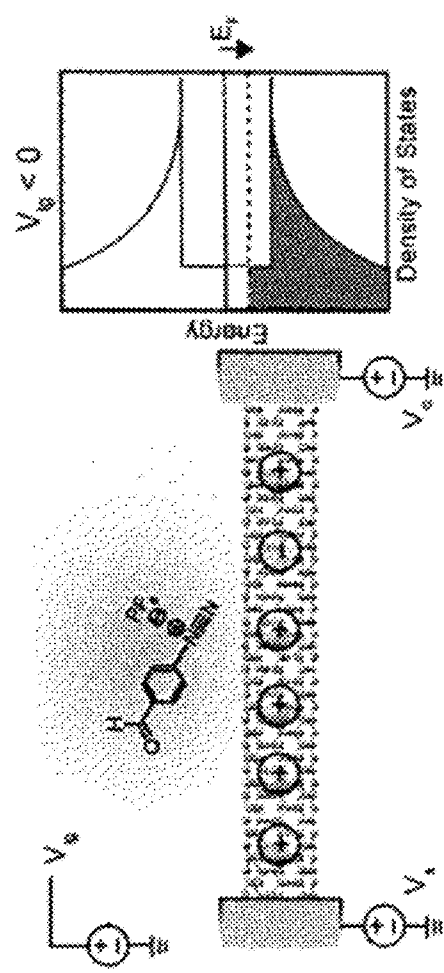
FIG. 12B illustrates a liquid-gate-potential-dependent diazonium reaction bias voltage when the liquid-gate potential is negative.

The extent of electron transfer, which leads to the formation of aryl radicals, is dependent on the electron density near the Fermi energy of the nanotube. Hence, the diazonium reactivity can be controlled through the applied $V_{lg}$, which modulates this Fermi level. The bias voltage $V_{lg}$ can be varied to promote or inhibit the reaction between (a) the diazonium salt solution and (b) the CNT. For example, FIG. 12A illustrates a bias voltage $V_{lg}$-induced diazonium reaction on the CNT. The hexafluorophosphate ($PH_6$) counterion provides stability to the FBDP molecule. An aldehyde group opposite to the diazonium cation is used for the DNA conjugation. In FIG. 12A, $V_{lg}$ is positive relative to the CNT surface, which shifts up the Fermi level ($E_f$) of the m-SWCNT, promoting spa defect generation by donating the electrons to the positively-charged $N_2$ group of the FBDP to form an aryl-radical. In FIG. 12B, $V_{lg}$ is negative and $E_f$ is shifted down, which halts the reaction as the population of electrons near the Fermi level is reduced.

Figure 13A:
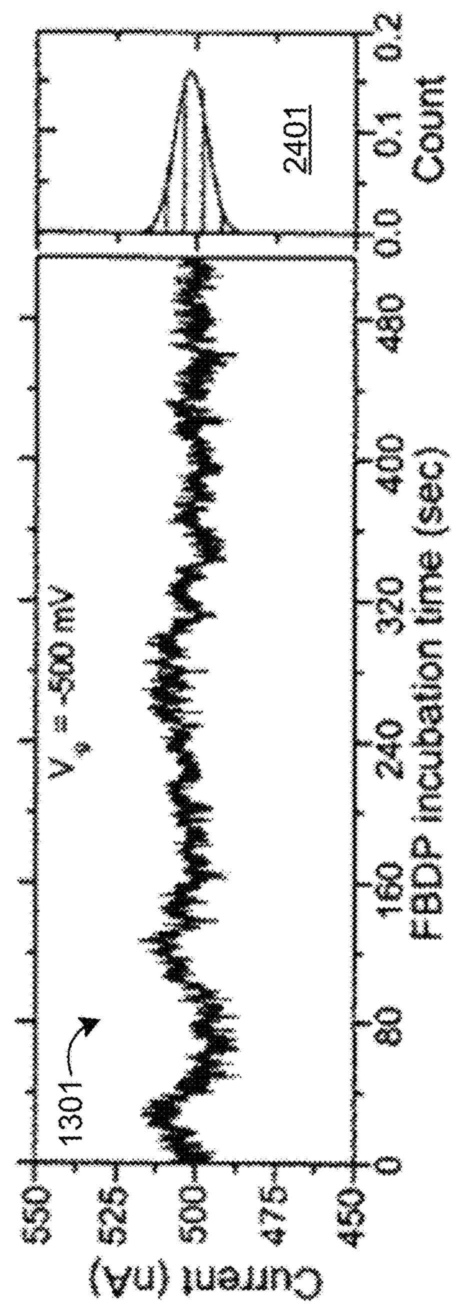
FIGS. 13A and 13B are current-time graphs of two representative spin-cast devices with a fixed liquid-gate potential of −500 mV and 0 V, respectively, and a fixed Vsd of 50 mV in the presence of FBDP solution at micro-molar concentrations.
Figure 13B:
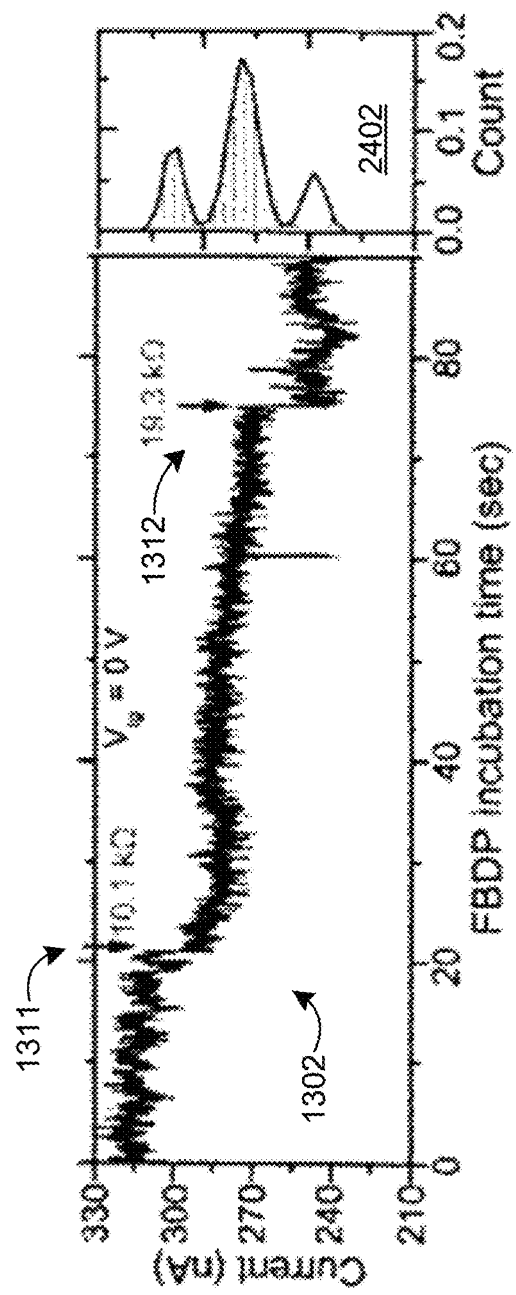

The effects of the applied $V_{lg}$ on reaction kinetics can be studied by examination of current-time (I-t) recordings (collected at 25 kSps) of two representative spin-cast devices with a fixed $V_{lg}$ of −500 mV and 0 V and a fixed $V_{sd}$ of 50 mV in the presence of FBDP solution at micro-molar concentrations, as illustrated in FIGS. 13A and 13B, respectively. At $V_{lg}$ of −500 mV after introducing a 6 μM FDBP solution, an m-SWCNT device exhibits a single current level with no discernible current drops for the entire recording time (515-sec) after FBDP exposure. Without being bound by theory, this can be attributed to inhibiting the diazonium reaction at this $V_{lg}$ by making holes the dominant charge carrier in the CNTs. A normalized histogram 1301 shows a single Gaussian distribution of the current level.

Returning to FIG. 11, after step 1160, flow chart 1100 proceeds to either step 1170 via placeholder B or to step 1180 via placeholder C. In step 1170, the bias voltage $V_{lg}$ is applied at a reaction potential (e.g., −300 mV or higher) for a predetermined time period. During the predetermined time period (or at the end), a point defect is formed in a portion of the CNT in step 1172. After the predetermined time period, the bias voltage $V_{lg}$ is adjusted to a non-reactive potential (e.g., −500 mV or lower) in step 1174 to inhibit further reaction between the CNT and the diazonium salt solution. In some embodiments, $V_{lg}$ is initially set to inhibit the reaction, then $V_{lg}$ is adjusted to promote the reaction for a predetermined time period, and then $V_{lg}$ returns to a non-reactive potential (e.g., to the initial value) to inhibit the reaction. In some embodiment, the bias voltage of the solution can be controlled using a reference electrode and $V_{lg}$ for each CNT is equal to the voltage of the reference electrode.

In step 1180, the bias voltage $V_{lg}$ is applied at a reaction potential (e.g., −300 mV or higher). Unlike in step 1170, the bias voltage $V_{lg}$ is not applied for a predetermined time period. Instead, the electrical current through the CNT is monitored in real time in step 1182. When a point defect is formed on a portion of the CNT in step 1184, the electrical current through the CNT exhibits a discrete drop in current. When this discrete current drop is detected in step 1186, the bias voltage $V_{lg}$ is lowered to a non-reactive potential (e.g., −500 mV or lower) to inhibit additional reaction between the CNT and the diazonium salt. In some embodiments, $V_{lg}$ is initially set to inhibit the reaction, then Vlg is adjusted to promote the reaction until a reaction is detected, and then Vlg returns to a non-reactive potential (e.g., to the initial value) to inhibit the reaction. In an alternative embodiment, another change in the electrical properties of the CNT can be monitored in real time in step 1182, such as an increase in the CNT'S resistance or a decrease in its conductivity, which can trigger the lowering of the bias voltage Vlg to a non-reactive potential in step 1184.

After steps 1174 and 1186, flow chart 1100 proceeds to step 1190 via placeholder D. In step 1190, the reagent (e.g., diazonium salt solution) is rinsed from the substrate (e.g., semiconductor substrate), for example using deionized water. The non-reaction potential can optionally be applied to the CNT during step 1190 to inhibit additional reaction between the CNT and the diazonium salt. In step 1192, a biomolecule (e.g., ssDNA) is attached to the defect site. Flow chart 1100 also proceeds through steps 1190 and 1192 after step 1150 via placeholder A.

For example, when $V_{lg}$ is fixed at 0 V, an m-SWCNT device exhibits discrete current levels 90-sec after exposure to a 10 μM FBDP solution (FIG. 13B). A normalized histogram 2402 characterizing the I-t recordings of this device reports two discrete, resolved/quantized current levels. In this experiment, the initial resistance of one device was 159.5 kΩ, and the resistance changes (ΔR) associated with the two current drops were quantified as 10.1 kΩ for the first drop 1311 and 19.3 kΩ for the second current drop 1312 on an m-SWCNT. In a Landauer formulation, these resistance drops result from reduced transmission (increased scattering) due to the addition of the defects in the otherwise largely ballistic nanotube dominated initially by contact resistance. At higher defect densities, transport changes from ballistic to localized with very significant increases in resistance steps during the FBDP incubation.

Modulation of $V_{lg}$ can be further used to halt the reaction. During the FBDP incubation, $V_{lg}$ (which begins at −500 mV) for each individual device is increased by +50 mV steps every ten seconds until one discrete downward step of current is detected. Within ten seconds after this defect generation is detected, $V_{lg}$ is switched back to −500 mV to halt further reactions. Device conductance is continuously monitored (while holding $V_{lg}$ at −500 mV) until the FBDP solution is flushed from the device to ensure that the single defect status remains unchanged as residual reagent is purged. m-SWCNTs were shown to be more susceptible to conjugation with aryl radicals than s-SWCNTs; in particular, m-SWCNTs are better able to stabilize the transition state through electron donation and are consequentially more reactive in aryl-radical reactions due to their finite electron density at the Fermi level.

The reaction potential and predetermined time period can be determined statistically to yield the desired point functionalization. The functionalization efficiency can be tuned through both functionalization time (the predetermined time period) and concentration of diazonium molecules in solution. For example, the concentration of diazonium molecules and the solution potential can be selected such that the predetermined time period is about 30 seconds to about 10 minutes, or any time or time range therebetween.

Figure 14A:
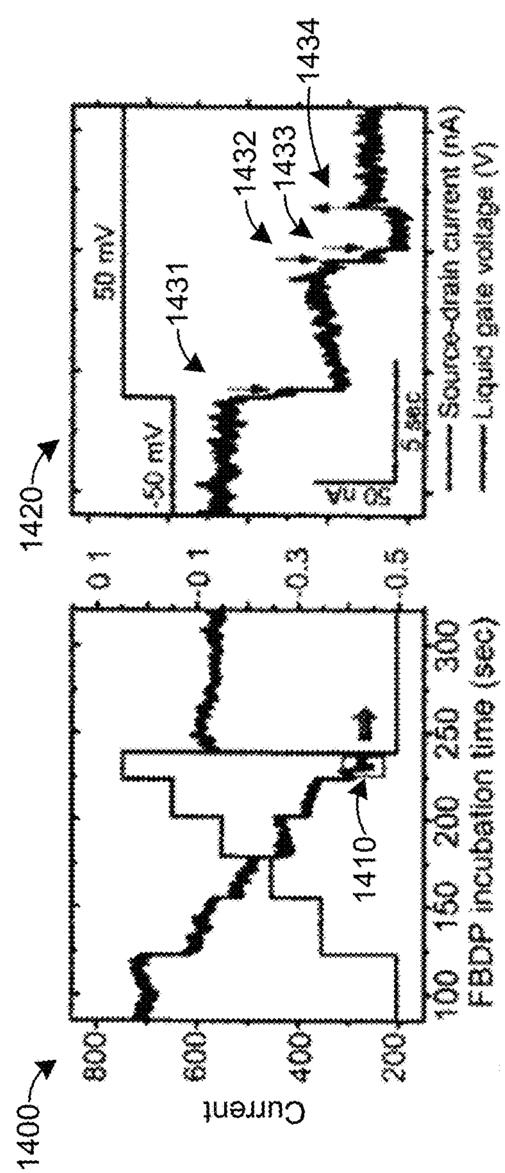
FIGS. 14A, 14B, and 14C are current-time graphs of feedback-controlled diazonium reaction for single-point functionalization as a function of liquid-gate-potential.

In some embodiments, electrochemical surveillance of the reaction can also detect unstable or reverse reactions on the CNT sidewall. In one functionalization trial, one upward current step after three serial step-wise drops induced at $V_{lg}$ of 50 mV was detected indicating a detachment of the unstable isolated aryl defect, as illustrated in FIG. 14A. Desorption of isolated aryl groups is possible if a remaining radical localizes near the defect site. Indeed, a rapid transition of current indicating diffusion and desorption dynamics of a short-lived single defect can be discerned. This unstable aryl radical can promote a second reaction to form stable aryl pairs when electrons are donated from the carbon nanotube. Most defect generation reactions resulted in stable products.

Feedback-controlled diazonium reaction for single-point functionalization can be employed. Initially, a liquid gate potential $V_{lg}$ of −500 mV is applied and subsequently increased to promote the reaction. When a downward current step is detected, $V_{lg}$ is immediately switched back to −500 mV to halt the reaction. Overlaid I-t and $V_{lg}$-t records of Device A1 during FBDP exposure, in which a device is exposed to 73 μM FBDP solution at $V_{sd}$ of 100 mV, is illustrated in graph 1400 in FIG. 14A. A zoomed-in view of box 1410 in graph 1400 $V_{lg}$ is illustrated in graph 1420 which indicates that $V_{lg}$ reached the threshold reaction potential, in which three consecutive downward steps 1431-

1433 and one upward step 1434 are monitored while holding $V_{lg}$ at 50 mV for approximately 15 seconds, indicating a net of two ultimate spa defects. The upward step 1434 corresponds to the detachment of the unstable isolated aryl defect.

Figure 14B:
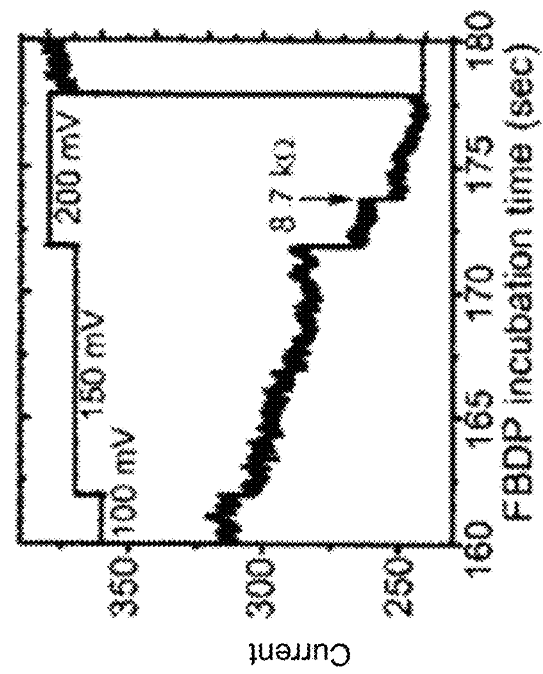
Figure 14C:
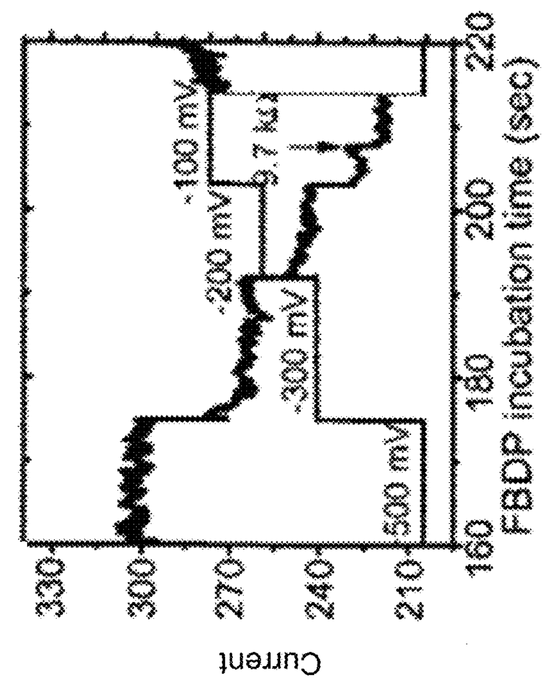

Representative stable first and second single-defect devices are shown in FIGS. 14B and 14C, respectively. The first device is exposed to 72 μM FBDP solution at $V_{sd}$ of 50 mV. A single downward step for the first device, corresponding to a resistance change of 8.7 kΩ, is detected within a few seconds after $V_{lg}$ reaches 200 mV, as illustrated in FIG. 14B. The second device is exposed to 6 μM FBDP solution at $V_{sd}$ of 50 mV. A single downward step for the second device, corresponding to a resistance change of 9.7 kΩ, after $V_{lg}$ reaches −100 mV, as illustrated in FIG. 14C. Subsequent downward or upward steps are not observed after this single-defect generation.

The stability of the functionalized point defect can be determined by calculating conductance changes before and after FBDP exposure. Compared to the initial value of $I_{on}$ at $V_{lg}$ of −500 mV, single-point-defected devices exhibited average conductance changes of 29.8±16.9%. On the other hand, devices with two defect sites exhibited conductance changes of 23.5±19.1%. No positive correlation is observed between the number of defects and the resulting reduced conductance at $V_{lg}$ of −500 mV. The relatively large variance in conductance associated with a single defect can be attributed to differences in the geometric configuration of the defect. As expected, the non-functionalized devices showed conductance changes of 0.03±0.05%, indicating that initial conductance was retained after FBDP exposure.

Example 2—Estimation of Conjugation Yield by Sensing Single-Molecule DNA Melting Dynamics To demonstrate the functioning of the spin-cast smFETs as single-molecule transducers, the single spa defect sites created in each device are covalently conjugated to an amine-modified 20-mer single-stranded DNA (ssDNA). Since spin-cast deposition results in surface-bound CNT devices, substrate-charge-trap-induced random telegraph signals (RTS) can occur. In some cases, devices display significant RTS at some point up to and including probe conjugation, and these devices can be excluded from further use.

It has been demonstrated that smFETs are capable of characterizing DNA hybridization and melting kinetics by temporal analysis of the resulting RTS and that a positive $V_{lg}$ is able to promote the molecular dissociation. RTS is observed with two discrete conductance levels (high and low) which correspond to the hybridized and melted state of the probe molecule, respectively.

Figure 15A:
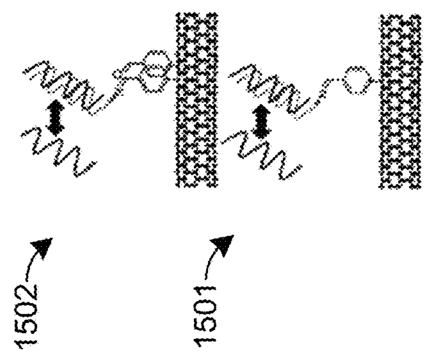
FIG. 15A is a diagram of a device that includes two defects and a device that includes a single defect.

A similar experiment can be performed to validate single-molecule sensing capabilities of the devices fabricated. After tethering the 20-mer probe DNA to the defect site, a solution containing fully complementary target DNA (100 nM) was introduced at a fixed temperature (40° C.), close to the theoretical melting temperature of $T_m$=49.7° C. while holding $V_{lg}$ at 400 mV. It has been previously shown that the electrostatic force induced by a positive $V_{lg}$ lowers the effective melting temperature, decreasing DNA hybridization rate ($k_{hyb}$) and increasing DNA melting rate ($k_{melt}$). I-t series were monitored at several liquid gate potential ($V_{lg}$) to modulate DNA dissociation dynamics. I-t traces for two different devices, one having two defects (device 1502 in FIG. 15A) and one having a single defect site (device 1501 in FIG. 15A), are independently monitored, and active RTS is detected at $V_{lg}$ of 400 mV.

Figure 15B:
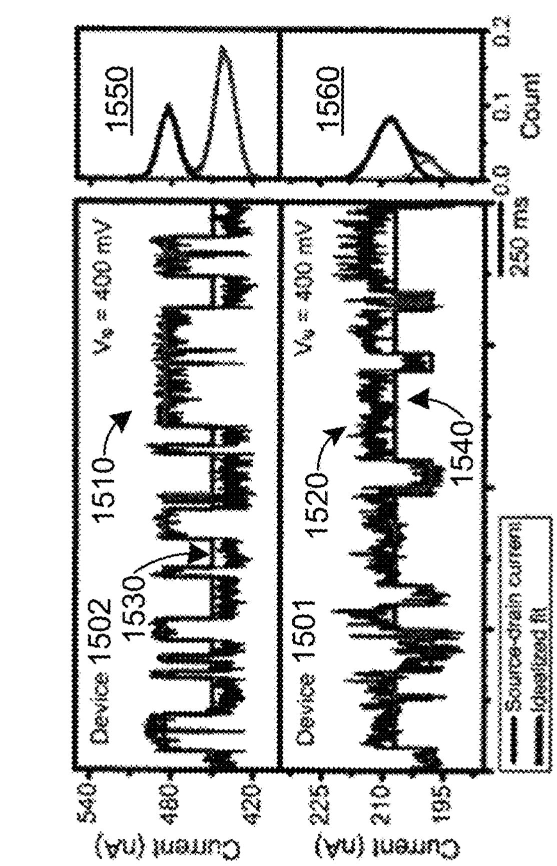
FIG. 15B illustrates current-time graphs and histograms of the devices illustrated in FIG. 15A.

The histograms of 60-sec I-t traces show two distinct conductance levels, as illustrated in FIG. 15B. In contrast, only one conductance level (and no RTS) was evident in two control experiments, one in which no target DNA is present and one in which a non-complementary 20-mer target DNA is present. In FIG. 15B, the total recording time is 180 seconds, and a representative two-second-length trace 1510, 1520 of the raw source-drain current for devices 1502, 1501, respectively, is overlaid with an idealized fit 1530, 1540, respectively. Corresponding source-drain current histograms 1550, 1560 of devices 1502, 1501, respectively, are plotted by counting the current in 60-second-length traces 1510, 1520 which are fit by two Gaussian distributions. Counts of the histograms 1550, 1560 are normalized by dividing by sum of total counts.

Figure 15C:
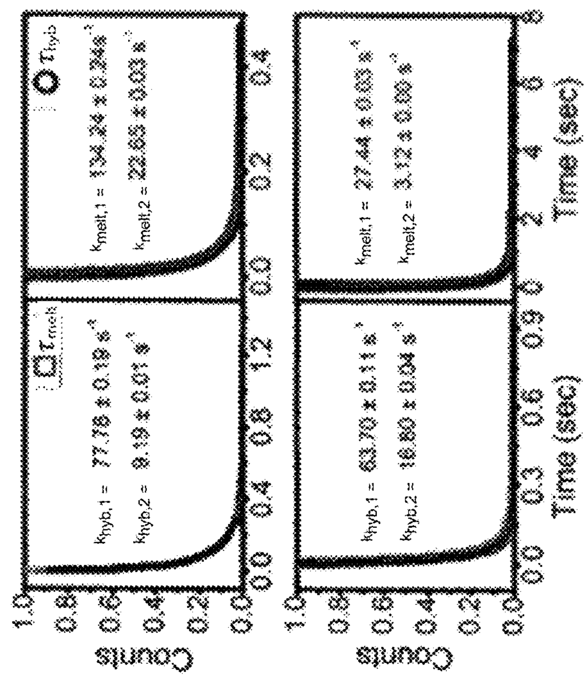
FIG. 15C illustrates double-exponential fits to the histograms illustrated in FIG. 15B.

An idealized trace, resulting from fits to the raw data using an iterative detection algorithm, can be used for subsequent temporal analysis. I-t traces can be fit to a two-state model to determine dwell times in the hybridized ($\tau_{hyb}$) and melted states ($\tau_{melt}$). A double-exponential fit to the resulting histograms can determine the rate constants ($k_{hyb}$) and ($k_{melt}$), as illustrated in FIG. 15C. $k_{hyb}$ is mainly determined by the diffusion of target to the probe and is a strong measure of target concentration. This diffusion process can be one-dimensional (1D) along the surface or three-dimensional (3D) from solution to the device. For the 100 nM concentration, the faster $k_{hyb}$ corresponds to the 3D diffusion and is used in subsequent analyses. The two different $k_{melt}$ values are also associated with 1D and 3D diffusion, in which the faster corresponds to 3D diffusion and is chosen for subsequent analysis. The equilibrium $\tau_{melt}$ constant ($K_{eq}$), determined by calculating the ratio of $k_{hyb}$ to $k_{melt}$, is close to one (1) at $V_{lg}$ of 400 mV for the fully-complementary target DNA at 40° C. Here, the resulting $K_{eq}$ values are in good agreement with the estimation.

The Schiff base reaction between the amine-modified ssDNA probe and aldehyde group of FBDP also has a finite yield. As a result, a two-point-functionalized device can tether two, one, or no probes. The device 1502 that has two defect sites, for example, shows two discrete conductance states in the presence of a fully-complementary target DNA solution. The device 1501 has one defect site also shows two discrete states in the presence of a fully-complementary target DNA solution.

These multiple-conductance-state transitions are attributed to the fact that two probe DNAs are attached to device 1501.

The foregoing merely illustrates the principles of the disclosed subject matter. Various modifications and alterations to the described embodiments will be apparent to those skilled in the art in view of the teachings herein. It will be appreciated that those skilled in the art will be able to devise numerous modifications which, although not explicitly described herein, embody its principles and are thus within its spirit and scope.

What is claimed is:

1. A method of making an integrated circuit for a single-molecule nucleic-acid assay platform, comprising:

adhering a carbon nanotube to a surface of a transfer film;

placing the surface of the transfer film on a CMOS integrated circuit;

releasing the carbon nanotube from the transfer film; and forming a pair of post-processed electrodes proximate opposing ends of the carbon nanotube, the post-processed electrodes electrically connecting the carbon nanotube to the CMOS integrated circuit.

2. The method of claim 1, wherein the transfer film comprises gold or a polymer.

3. The method of claim 1, further comprising chemically removing the transfer film to release the carbon nanotube.

4. The method of claim 3, wherein:

chemically removing the transfer film comprises wet etching the transfer film, and the transfer film comprises gold.

5. The method of claim 3, wherein chemically removing the transfer film comprises soaking the CMOS integrated circuit in an organic solvent, and the transfer film comprises a polymer.

6. The method of claim 1, further comprising:

placing the nanotube on a transfer substrate;

depositing the transfer film on the transfer substrate; and lifting off the transfer film from the transfer substrate, the transfer film comprising the nanotube.

7. The method of claim 6, further comprising growing the nanotube on the transfer substrate.

8. The method of claim 7, wherein:

the transfer film comprises a polymer, and depositing the transfer film comprises spinning the polymer onto the transfer substrate.

9. The method of claim 7, wherein:

the transfer film comprises gold, and depositing the transfer film comprises physical vapor depositing and/or electroplating the gold onto the transfer substrate.

10. The method of claim 1, wherein forming the pair of post-processed electrodes comprises depositing titanium, palladium, gold, platinum, silver, chromium, and/or aluminum on a pair of surface-exposed electrodes.

11. The method of claim 1, wherein forming the pair of post-processed electrodes comprises etching away a pair of surface-exposed electrodes and replacing the pair of surface-exposed electrodes with a pair of electrodes that comprise titanium, palladium, gold, platinum, silver, chromium, and/or aluminum.

12. The method of claim 1, further comprising forming one or more reference electrodes on the CMOS integrated circuit to allow control of an electrolytic gating potential.

13. The method of claim 12, wherein the one or more reference electrodes comprise platinum, palladium, and/or silver.

14. The method of claim 13, wherein:

the one or more reference electrodes comprise a silver electrode, and the silver electrode is converted into a silver-chloride electrode.

15. A method of making an integrated circuit for a single-molecule nucleic-acid assay platform, comprising:

spraying a carbon nanotube suspension on the surface of the CMOS integrated circuit, the carbon nanotube suspension comprising a liquid and carbon nanotubes;

evaporating the liquid from the carbon nanotube suspension to deposit the carbon nanotubes on the surface of the CMOS integrated circuit; and forming a pair of post-processed electrodes proximate opposing ends of one or more of the carbon nanotubes, the post-processed electrodes electrically connecting the one or more carbon nanotubes to the CMOS integrated circuit.

16. The method of claim 15, further comprising rasterizing the CMOS integrated circuit and/or a spray nozzle during the spraying.

17. The method of claim 15, further comprising spraying the carbon nanotube suspension from a print head nozzle or an ultrasonic nozzle.

18. The method of claim 17, further comprising heating the CMOS integrated circuit to evaporate the liquid from the carbon nanotube suspension.

19. The method of claim 15, wherein forming the pair of post-processed electrodes comprises etching away a pair of surface-exposed electrodes and replacing the pair of surface-exposed electrodes with a pair of electrodes that comprise titanium, palladium, gold, platinum, silver, chromium, and/or aluminum.

20. The method of claim 15, further comprising forming one or more reference electrodes on the CMOS integrated circuit to allow control of an electrolytic gating potential.

21. The method of claim 20, wherein the one or more reference electrodes comprise platinum, palladium, and/or silver.

22. The method of claim 21, wherein:

the one or more reference electrodes comprise a silver electrode, and the silver electrode is converted into a silver-chloride electrode.

23. A method of making an integrated circuit for a single-molecule nucleic-acid assay platform, comprising:

forming a pair of electrodes on opposing ends of a carbon nanotube, the electrodes electrically connecting the carbon nanotube to a CMOS integrated circuit;

exposing the carbon nanotube to a diazonium salt solution; and applying a reaction liquid-gate bias voltage that promotes a reaction between (a) the diazonium salt solution and (b) the carbon nanotube to form a point defect on a portion of the carbon nanotube.

24. The method of claim 23, further comprising:

applying an initial liquid-gate bias voltage to inhibit the reaction; and adjusting the liquid-gate bias voltage to the reaction liquid-gate bias voltage to promote the reaction.

25. The method of claim 24, further comprising:

monitoring an electrical current through the carbon nanotube while applying the reaction liquid-gate bias voltage; and detecting a discrete drop in the electrical current through the carbon nanotube; and returning the liquid-gate bias voltage to the initial liquid-gate bias voltage after detecting the discrete drop.

26. The method of claim 24, further comprising:

applying the reaction liquid-gate bias voltage for a predetermined time period; and returning the liquid-gate bias voltage to the initial liquid-gate bias voltage at the end of the predetermined time period.

27. The method of claim 24, further comprising:

exposing the carbon nanotube to the diazonium salt solution for a predetermined time period; and rinsing the surface of the CMOS integrated circuit to halt a reaction between (a) the diazonium salt solution and (b) the carbon nanotube to form the point defect.

28. The method of claim 24, further comprising depositing a photoresist or an e-beam resist on a portion of the surface of the CMOS integrated circuit prior to exposing the carbon nanotube to the diazonium salt solution to define an isolated exposed region on the surface of the CMOS integrated circuit for a reaction between the carbon nanotube and the diazonium salt solution.

29. The method of claim 23, further comprising:

exposing the carbon nanotube to the diazonium salt solution for a predetermined time period; and rinsing the surface of the CMOS integrated circuit to halt a reaction between (a) the diazonium salt solution and (b) the carbon nanotube to form the point defect.

30. The method of claim 23, further comprising depositing a photoresist or an e-beam resist on a portion of the surface of the CMOS integrated circuit prior to exposing the carbon nanotube to the diazonium salt solution to define an isolated exposed region on the surface of the CMOS integrated circuit for a reaction between the carbon nanotube and the diazonium salt solution.

* * * * *